(12) United States Patent
Ashe et al.

(10) Patent No.: US 7,771,664 B2
(45) Date of Patent: Aug. 10, 2010

(54) REACTOR HEAT TRANSFER SYSTEMS

(76) Inventors: Robert Ashe, 6 Christchurch Crescent, Radlett, Hertfordshire (GB) WD7 8AH; David Charles Morris, Oak View 1 Eversly Close, Appleton, Warrington, Cheshire (GB) WA4 5NW ( * ) Notice: Subject to any disclaimer, the term of this patent is extended or adjusted under 35 U.S.C. 154(b) by 843 days.

(21) Appl. No.: 10/475,440

(22) PCT Filed: Apr. 24, 2002

(86) PCT No.: PCT/EP02/04646

§ 371 (c)(1),
(2), (4) Date: May 4, 2004

(87) PCT Pub. No.: WO02/087752

PCT Pub. Date: Nov. 7, 2002

(65) Prior Publication Data

US 2004/0202587 A1    Oct. 14, 2004

(30) Foreign Application Priority Data

Apr. 27, 2001   (GB) ................................. 0110299.5

(51) Int. Cl.
*G05D 23/00* (2006.01)
*G05D 7/00* (2006.01)
*B01J 19/00* (2006.01)
*F28D 21/00* (2006.01)

(52) U.S. Cl. ...................... 422/109; 422/105; 422/110; 422/198; 422/202

(58) Field of Classification Search ................. 422/198, 422/197, 201, 202, 105, 109, 110
See application file for complete search history.

(56) References Cited

U.S. PATENT DOCUMENTS

| 403,936 A | * | 5/1889 | Halsey | ........................ 165/101 |
| 2,590,436 A | | 3/1952 | Luten, Jr. | ......................... 23/1 |

(Continued)

FOREIGN PATENT DOCUMENTS

| DE | 4223805 A1 | * | 1/1993 |
| DE | 19931063 A1 | | 1/2001 |
| EP | 0737511 A1 | | 10/1996 |

OTHER PUBLICATIONS

Abstract of Burst et al. DE-4223805 A1.*

(Continued)

*Primary Examiner*—Walter D Griffin
*Assistant Examiner*—Lessanework Seifu
(74) *Attorney, Agent, or Firm*—Ohlandt, Greeley, Ruggiero & Perle, LLP

(57) ABSTRACT

A reaction system in which a heat transfer fluid is carried through a process fluid in a conduit and the heat transfer surface area between the conduit and the process fluid can be varied according to the heat generated or absorbed by the reaction as determined by the temperature change in the heat transfer fluid across the reaction and the mass flow of the heat transfer fluid through the conduit.

11 Claims, 13 Drawing Sheets

U.S. PATENT DOCUMENTS

| | | | | |
|---|---|---|---|---|
| 3,047,274 A | * | 7/1962 | Wilson | 165/281 |
| 3,318,376 A | * | 5/1967 | Vihl | 165/169 |
| 3,869,914 A | * | 3/1975 | Koehler et al. | 374/33 |
| 5,638,898 A | * | 6/1997 | Gu | 165/160 |
| 5,762,879 A | | 6/1998 | Nomura et al. | 422/109 |
| 5,779,994 A | | 7/1998 | Küpper et al. | 422/197 |

OTHER PUBLICATIONS

Perry, R.H.; Green, D.W. (1997). Perry's Chemical Engineers' Handbook (7th Edition). McGraw-Hill. Section 11, pp. 1-20.*

Horak et al., "*Temperature Control in a Chemical Reactor Through Variable Area of the Heat Transfer Surface. Experimental Data*", Collection Czechoslovak Chem. Commun. vol. 47, 1982, pp. 446-453.

GB International Search Report Application No. GB0110299.5, dated Aug. 7, 2001.

International Search Report Application No. PCT/EP02/04646, dated Aug. 19, 2002.

* cited by examiner

REACTOR HEAT TRANSFER SYSTEMS

FIELD OF THE INVENTION

The present invention relates to reaction systems and in particular reaction systems embodying improved heat transfer. Reaction systems may involve physical and/or chemical changes. Chemical reactions involve chemical change such as in the reaction of two or more molecules to produce a new molecule including polymerisation, in the breakdown of molecules into two or more molecules. Physical reactions involve a change of state such as in crystallisation, precipitation, evaporation, melting, solidification and the like. Certain reactions can involve both chemical and physical change.

The invention is concerned with improving the ability to monitor the progress of physical and/or chemical reactions, it is also concerned with improving the control of reaction systems through the improved monitoring. The improved control that is provided by the present invention enables the production of materials of higher quality and purity, it enables more efficient use of reaction equipment and can further improve the efficiency of the equipment so that shorter reaction times are needed to obtain a given amount of material from a given amount of starting materials. Another advantage is that smaller reactors may be used to produce a given volume of material.

DISCUSSION OF THE BACKGROUND ART

Many reactions are hazardous and care needs to be taken to ensure no accidents. The more accurate and more timely monitoring of the reaction provided by this invention enables reactions to be performed within stricter limits. This enhances safety and can reduce the reaction inefficiencies that, hitherto, were an inherent shortcoming of the manufacturing process. Furthermore, the ratios of reactants can be optimised reducing the need for excess reactants to ensure completion of a reaction.

Reactions whether they be physical, chemical or both generate or absorb heat and there is therefore a heat change across the reaction. The theoretical heat generated or absorbed in a particular reaction is known from established information. The actual heat generated or absorbed during the course of a reaction could therefore, in theory, be a useful measure to determine reaction efficiency in the case of steady state reactions and reaction progress in the case of batch reactions.

By way of an illustration of the theory, a typical chemical synthesis step will be considered. Two reagents (A and B) react together to form a new compound (C) as follows:

A+B C where
A=kmol of A
B=kmol of B
C=kmol of C

The heat generated by this reaction is established according to the formula:

$$Q = Hr \cdot C \text{ (kJ)}.$$

where
Hr=heat of reaction per kmol of C produced (kJ/mol)
C=kmol of component C produced (kmol)

The value of Hr may be determined from theoretical data or laboratory calorimeters.

Currently the heat data described may be used in a variety of ways.

For any reaction, the maximum theoretical heat liberation can be calculated as follows:

$$Q' = Hr \, C' \text{ (kJ)}$$

where
Q'=maximum theoretical heat generated (kJ)
Hr=heat of reaction per kmol of C produced (kJ/kmol)
C'=maximum theoretical yield of component C (kmol)

The maximum theoretical yield C' is based on the assumption that one or both of the feed components (A and B) are completely consumed.

If the heat of reaction is measured during a process, the quantity of component C synthesised at any time is as follows:

$$C = Q/Hr \text{ (kmol)}$$

where
C=quantity of C produced (kmol)
Q=heat measured during the reaction (kJ)
Hr=heat of reaction per kmol of C produced (kJ/kmol)

Thus the total mass of C can be calculated by knowing the total heat absorbed or liberated and the heat of reaction (or crystallisation etc).

The expected theoretical yield of C is known from the quantity of reactants present and the stoichiometry of the process. Thus from the information above, the percentage conversion can be determined from the equation below.

$$\text{} = C/C' \times 100$$

where  = percent conversion
$C$ = quantity of $C$ produced (kmol)
$C'$ = maximum theoretical yield of component $C$ (kmol)

In batch reactions, percent conversion ( ) provides an effective means of identifying reaction end point and/or optimum reaction ratios. This can be used to reduce manufacturing time, improve plant utilisation, and reaction efficiency.

The present invention may also be used in laboratory activities such as in laboratory calorimetry. Use of the techniques of the present invention can reduce or eliminate the errors in conventional jacketed calorimetric measurement and simplifies temperature control during calorimetric measurement. In this way a quicker and more accurate method for the determination of theoretical Hr is provided. Unlike optical analytical devices, the calorimetric data is measured with inherently simple instruments which are not impaired by common process effects (fouling, composition change, temperature variation, mixed phases etc). Unlike optical analytical devices calibration of the calorimetric instruments is not product specific and instruments can be tested and calibrated on any fluid.

In continuous (plug) flow reactors, reaction efficiency ( ) provides a parameter for controlling feed rate to the reactor and controlling process conditions. In this way it is possible to run conventional batch processes in small-scale plug flow reactors. This benefits all aspects of the manufacturing process including lower capital cost for equipment, increased plant versatility, improved product yield, safer process conditions (through smaller inventories), greater product throughput and reduced product development time.

The ability to monitor reaction progress has an additional safety benefit for both small and large reactors. A system with online calorimetric data can instantly identify when unreacted compound is accumulating in the reactor. This reduces the risk of runaways due to accumulation of unreacted chemicals.

The design of reactors in common industrial use is however inherently unsuitable for measuring calorimetric data and thus the techniques described remain theoretical.

Chemical reactors in common use in, for example, the pharmaceutical and fine chemical industries fall into four main categories. Standard batch reactors in which reagents are mixed in a stirred vessel in which heat is added or removed by means of heat transfer fluid recirculating though an external jacket. These are the most commonly used reactors for small-scale organic and inorganic synthesis reactions. Batch reactors with internal coils, which are a variation on the standard batch reactor and have additional heat transfer surfaces within the body of the liquid. These reactors are used for general-purpose batch reactions where higher heat loads are encountered. Loop reactors in which reactants are pumped through an external heat exchanger and returned to the vessel. These are commonly used for gas/liquid reactions in which case the liquid is returned to the reactor via a spray nozzle to create a high gas/liquid interfacial area. Continuous reactors in which reactants are pumped through a heat exchanger under steady state conditions. These are generally used for larger scale manufacturing processes with long product runs.

The heat transfer characteristics of the four types of reactors described above have three common features:
  i. The heat transfer fluid is circulated through the heat exchangers at high velocity to maintain favourable heat transfer coefficients. In the case of jacketed reactors, this is achieved by injecting the heat transfer fluid into the jacket at high velocities using nozzles or diverting flow around the jacket with baffles. In some instances, coils for the flow of heat transfer fluid are welded to the outside wall of the reactor vessel.
  ii. High mass flow rates of heat transfer fluid are employed to maintain a good average temperature difference between the heat transfer fluid and the process fluid.
  iii. The heat transfer area is fixed and temperature control of the process fluid is achieved by varying the temperature of the heat transfer fluid. In some cases limited scope exists for increasing or decreasing the heat transfer area.

The features described above represent good design practice for achieving a flexible and optimised heat transfer capability within the reactor. However, these features do not lend themselves to measuring the quantity of heat generated or liberated. This deficiency is illustrated by reference to the chemical reaction between reagents A and B as discussed above. (It should be noted that the example is not limited to chemical reactions and is equally applicable to other chemical and physical processes).

When the two reagents (A and B) react together to form C, heat is liberated. The heat liberated per second can be expressed as follows:

$$q = Hr \cdot c \text{ (kW)}$$

where
  q=heat liberated per second (kW)
  Hr=heat of reaction per kmol of C produced (kJ/kmol)
  c=kmols of component C produced per sec (kmol/s)

If the process temperature remains constant the heat liberated (q) will be observed as a temperature rise in the heat transfer fluid according to the formula.

$$q = m \cdot Cp(t_{si} - t_{so})$$

where
  q=heat absorbed by the heat transfer fluid which is the heat liberated by the reaction (kW)
  m=mass flow rate of the heat transfer fluid (kg/s)
  Cp=specific heat of heat transfer fluid (kJ·kg$^{-1}$K$^{-1}$)
  $t_{si}$=temperature of heat transfer fluid in (° C.)
  $t_{so}$=temperature of heat transfer fluid out (° C.)

However, in order to determine q, the flow rate and temperature change of the heat transfer fluid ($t_{si}$–$t_{so}$) must be measured accurately. In the reactor examples described above, effective design favours high flow rates of heat transfer fluid. Often this leads to a temperature change of the heat transfer fluid ($t_{si}$–$t_{so}$) of less than 1° C. An IEC Class A RTD is one of the more accurate temperature measurement devices available. These devices have a tolerance of ±0.25° C. (the error on the installed device may be higher).

Thus for a temperature change of 1° C., the accuracy of heat measurement can be expected to be ±25% or worse. This would rise to 250% where the heat transfer fluid temperature changed by 0.1° C. This factor alone makes it virtually impossible to measure the heat of reaction in conventional reactors. Furthermore, on a conventional reactor, heat leaking out of the system via the non-process side of the jacket can create serious error.

Furthermore, conventional chemical reactors often have sluggish control systems which permit temperatures of the bulk material to cycle by a few degrees. In energy terms a few degrees change in temperature can represent a significant proportion of the overall energy release.

Furthermore the control speed is faster in that the ability to main the conduits at constant temperature permits a much higher correcting temperature on a newly opened conduit. The control is therefore faster and more accurate.

Conventional reactors offer acceptable heat transfer characteristics when the flow of heat transfer fluid is held at a good velocity. Since the heat transfer surface is limited to 1 or 2 discrete elements, the range (of energy liberated or absorbed) over which a useful service temperature rise ($t_{si}$–$t_{so}$) can be achieved is very limited. In a case where the energy release from the process is small, the temperature rise in the heat transfer fluid may be a fraction of a degree. In addition to this, the shaft energy of the heat transfer pump could be a high proportion of the total.

The limitations described above are common to all reactors (and evaporators, batch stills etc) used in the pharmaceutical, chemical and allied industries. Accordingly, when employing these reactors the heat generated or consumed by the reaction cannot be used to monitor the progress of a reaction within any degree of accuracy.

It has been proposed in U.S. Pat. No. 6,106,785 that the heat generated in a polymerisation reaction may be used to monitor the progress of the reaction. The system of U.S. Pat. No. 6,106,785 is however a coarse method for monitoring a reaction which involves employing an inferential sensor, whose concept is based on the observation that for polymerisation processes, the amount of heat released is proportional, albeit in a non-linear way, to the degree of the monomer conversion. According to U.S. Pat. No. 6,106,785 by careful calculation of the reactor's thermal balance on-line one can continuously infer the degree of conversion and use it for control. Once the actual degree of conversion can be determined and ultimately controlled, one can also control the cooling duty of the reactor and thus make it conform with the cooling capacity allotted to it by the plant scheduler. U.S. Pat. No. 6,106,785 is therefore concerned with optimising the use of heat transfer fluid and the addition of initiator/inhibitor within safe operating parameters.

In U.S. Pat. No. 6,106,785 the batch controller data is used directly to control the reactor mixture temperature by manipulating the incoming coolant flow and temperature. The data are fed into the inferential sensor, where they are used to infer the current value of the degree of monomer conversion.

In U.S. Pat. No. 6,106,785 the degree of conversion is not therefore measured directly, but it is inferred by dynamically evaluating the reactor heat balance. U.S. Pat. No. 6,106,785 therefore enables one to infer the degree of conversion from the dynamic evaluation of the reactor heat balance. The use of the degree of conversion replaces special sensors for feedback control with respect to the product quality (end-use) properties. The use of the degree of conversion also replaces physical time for the timing of process related operations like valve opening and closing, and enables control of the heat supply/removal, dosing of the reactants, and so forth. The use of the sensor is said to allow an increase in the accuracy of the prediction of the batch evolution and thus enables a more accurate prediction of the cooling need profile than that provided by the systems previously used.

In U.S. Pat. No. 6,106,785, the reaction mixture temperature and the integral heat rate are treated as two independent process variables. This approach is said to allow the user the freedom to specify batch recipes in a way that defines the evolutions of either variable during the batch run, and to execute them under tight, high performance control. Because the degree of monomer conversion is proportional to the integral heat rate for many important polymers including PVC, controlling the two variables is said to allow the user independent control over two basic determinants of products quality. According to U.S. Pat. No. 6,106,785 this control fully defines the heat release at every instant of the batch run, thus making it possible to better utilize the available cooling capacity through more reliable planning and scheduling. To control the temperature and integral heat rate independently, the proposed method manipulates the amount of heat added to or taken out of the reaction and the amounts of the initiator(s) and inhibitor added during the batch run.

Whilst these techniques bring benefits in optimising the use of the coolant they are not sufficiently accurate and discerning to enable sophisticated sensing and control of a reaction. The present invention provides the solution to this problem.

In our co-pending United Kingdom Patent Application 0110301.9, we describe and claim reactor systems which provide improved control over physical and/or chemical reactions. The present invention relates to United Kingdom Patent Application 0110301.9 in that it enables the improved control to be achieved over a wide range of operating conditions by the use of a variable heat transfer area between the process fluid and the heat transfer fluid. Our co-pending United Kingdom Patent Application 0110295.3 describes measurement systems which may be used with this invention.

SUMMARY OF THE INVENTION

Accordingly the present invention provides a reaction system in which the heat transfer fluid is carried in a conduit which is either part of the reactor vessel wall and/or passes through the process fluid and the heat transfer surface area between the conduit and the process fluid can be varied according to the heat generated or absorbed by the reaction as determined by the temperature change in the heat transfer fluid across the reaction and the mass flow of the heat transfer fluid through the conduit.

Whilst any form of conduit may be used for the heat transfer fluid, pipes, plates or coils are preferred and the invention will hereafter be described in relation to the use of a coil or coils.

In a preferred embodiment, the present invention provides a reaction system comprising a reactor containing a reaction process medium and a heat exchanger providing a conduit through which flows a heat transfer fluid wherein measurement of the flow rate and temperature change of the heat transfer fluid across the reaction is used to determine the heat generated or absorbed by the reaction system and that determination is used to control the heat transfer surface area between the conduit and the process fluid wherein i. the average temperature difference between the heat transfer fluid and the processes fluid is from 1 to 1000° C., preferably from 1 to 100° C.
ii. the temperature differential ($t_{si}-t_{so}$) of the heat transfer fluid across the reaction system is at least 0.1° C., preferably at least 1° C.
iii. the linear velocity of the heat transfer fluid is at least 0.01° C. meters/second, preferably at least 0.1 meters/second.

We have found that providing these criteria are satisfied measurement of the flow rate and temperature change of the heat transfer fluid across the reaction enables the heat generated or absorbed by the reaction system to be determined with a high degree of accuracy over a wide range of operating conditions. The determination may then be used to monitor and control the heat transfer surface area between the conduit and the process fluid and thus control the reaction with a high degree of accuracy.

In order for effective operation, the reaction system should preferably have the following characteristics:

a. The available surface area of the heat exchanger should be sufficient to ensure that a measurable temperature difference ($t_{si}-t_{so}$) is observed in the heat transfer fluid as it passes across the reactor. For the purposes of accuracy, a temperature difference of more than 0.1° C. is preferred, more preferably more than 1° C. (preferably more than 5° C., more preferably more than 10° C.).
b. A high temperature difference is preferably maintained between the process fluid and the inlet heat transfer fluid ($t_{si}$) to ensure that an accurately measurable service fluid temperature change ($t_{si}-t_{so}$) can be achieved and smaller heat transfer areas are required.
c. As far as possible, heat must only be transferred to or from the process fluid and not be transferred to other equipment or the environment.
d. The heat transfer fluid must always flow at a reasonable velocity. The velocity will vary with conduit, preferably coil, size and conditions but it is preferred that it is greater than 0.01 meters/second preferably greater than 0.1 meters/second, most preferably greater than 1 meters/second. Lower velocities will give slower temperature control response. Low velocities also give a higher ratio of thermal capacity (of the heat transfer fluid) to heat release rate. This will compound errors in the values of measured heats.
e. When used for batch processes or multi-purpose duties, the heat transfer equipment should be capable of stable operation over a wide range of energy release/absorption rates. The range will vary according to the nature of the reaction. In the case of batch reactions a very wide operating range will be required.

To satisfy condition c above, the heat exchanger is preferably immersed in the process fluid and should be fully insulated at all points other than where fully immersed in the process fluid. This ensures that all the heat gained or lost by the heat transfer fluid is transferred directly from and to the process fluid. This condition is most easily achieved by designing the heat exchanger as a coil or plate fully immersed in the process fluid.

It is further preferred that an optimal relationship between heat transfer surface area to heat transfer fluid flow capacity is provided. Such conditions exist when the heat transfer fluid (traveling at the desired linear velocity) provides an easily measured temperature change (such as 10° C.) without incurring excessive pressure drop. It should be noted that the optimum heat transfer conditions vary according to the properties of the process fluids and heat transfer fluids respectively.

In order to satisfy these criteria, the heat exchanger for the reactor is preferably a heat transfer coil, which preferably passes through the reaction fluid. The design of the coil is important to achieving the object of the invention and must be such that the heat transfer area matches the heat carrying capacity under specified conditions.

The techniques of the present invention may be used in systems in which the heat transfer fluid is straight through or recycled. We have found however that the system of the present invention is most effective when the heat transfer fluid is delivered at constant velocity and temperature.

The heat transfer area of a coil may be related to the flow carrying capacity of the liquid by using the formula $$U \cdot A \cdot LMTD = m \cdot Cp \cdot (t_{si} - t_{so}) \text{ (kW)}$$

where
U=overall heat transfer coefficient (kW·m$^{-2}$·K$^{-1}$)
A=heat transfer area (m$^2$)
m=mass flow rate of heat transfer fluid (kg/s)
LMTD=log mean thermal difference between service and process fluids (° C.)
Cp=specific heat of heat transfer fluid (kJ·kg$^{-1}$K$^{-1}$)
($t_{si}$-$t_{so}$)=temperature (° C.) change in the heat transfer fluid between inlet and outlet The area A is the area that is in contact with the process fluid.

This information may then be used to optimize the heat transfer from the heat transfer fluid to the heat transfer surface. This can be used to determine the optimum diameter to length relationship of an individual coil whereby high turbulence is achieved without incurring excessive pressure drop of heat transfer fluid through the heat exchanger (as shown by a high Reynolds number). Alternatively if the conduit is a plate the formula can be used to determine the optimum hydraulic path for the heat transfer fluid through the plate.

In order for effective operation it is preferred that
a. The temperature difference between the inlet heat transfer fluid and the process fluid should be large enough (e.g. 5-100° C.) to ensure that the heat transfer fluid undergoes a measurable temperature change (>1° C. or preferably greater than 10° C.) in its passage through the coil. The temperature change must not however be so high or low as to cause freezing, waxing out, boiling or burning of the process fluid.
b. The heat transfer area must be large enough to ensure that the heat transfer fluid undergoes a measurable temperature change (preferably >1° C. or more preferably greater than 10° C.) through the process fluid. Smaller temperature changes limit heat transfer capacity and accuracy. Higher temperature changes are desirable providing they do not cause freezing, waxing out, boiling or burning of the process fluid.
c. The linear velocity of heat transfer fluid must be reasonably high (preferably>0.1 m·s$^{-1}$) in order to maintain satisfactory control response and a good overall heat transfer coefficient.
d. The pressure drop of the heat transfer fluid flowing through the coil is from 0.001 to 20 or preferably 0.1 to 20 bar.

In practice, optimum coil lengths will vary according to the temperature differences employed and the thermodynamic and physical characteristics of the system. Calculating optimal coil length is an iterative process. A general-purpose device will be sized using conservative data based on fluids with low thermal conductivity and a low temperature difference between the reaction fluid and the heat transfer fluid. Each coil will have a limited operating range. Small variation in coil length can be accomplished by varying the shape of the coil such as by the provision of fins to increase surface area.

In the system of the present invention in which the heat transfer equipment is capable of stable operation over a wide range of energy releases, the system is such that the area of heat transfer may be varied according to the needs of the particular reaction (or stage of reaction). This may be conveniently accomplished by providing multiple heat transfer conduits such as pipes or coils each of which has a diameter and length relationship designed to provide a certain degree of heat transfer or plates with a surface area and hydraulic path for the heat transfer fluid designed to provide a certain degree of heat transfer. In the preferred multiple coil system, the coils may be brought into and out of operation as the needs of the reaction system dictates.

Alternatively the area of heat transfer may be varied by providing the reactor wall or a jacket for the reactor wall consisting of a series of conduits for the heat transfer fluid which can be brought into or out of operation as the needs of the reaction system dictates. In this way the heat exchanger is or forms part of the vessel wall. Similarly the heat exchanger may consist of a series of plates which can be brought into or out of operation as the needs of the reaction system dictates. The use of variable area to improve temperature control provides faster and more stable temperature control and response and also enables a fixed user defined heat flux.

Stable conditions in the open coils, particularly in calorimeters, give reduced interference due to temperature overshoot effects. Furthermore the control speed is faster in that the ability to maintain the conduits at constant temperature permits a much higher correcting temperature on a newly opened conduit. The control is therefore faster and more accurate.

Calorimetry refers to the measurement of heat entering or leaving a system. In the case of industrial processes, calorimetric data can be an extremely valuable guide to the health and progress of process operations. The variable area design delivers calorimetric data which is incomparably better than conventional systems for the following reasons:
I. In conventional heat exchangers, large externally imposed heat fluctuations are used to control the process temperature. This 'heat noise' combined with inherent control delay makes accurate calorimetry impossible. When using the variable area design, the externally imposed fluctuations are virtually eliminated and the control delays substantially reduced.
II. Not only does variable area deliver better temperature control, it continues to do so whilst calorimetry is being measured. This reduces the problem of error and complexity associated with variations in the system temperature.
III. The operating conditions can be set up to give a consistently high temperature change in the heat transfer fluid, without compromising temperature control performance. This enables accurate temperature data to be collected.

DETAILED DESCRIPTION OF THE PREFERED EMBODIMENT

Figure 1:
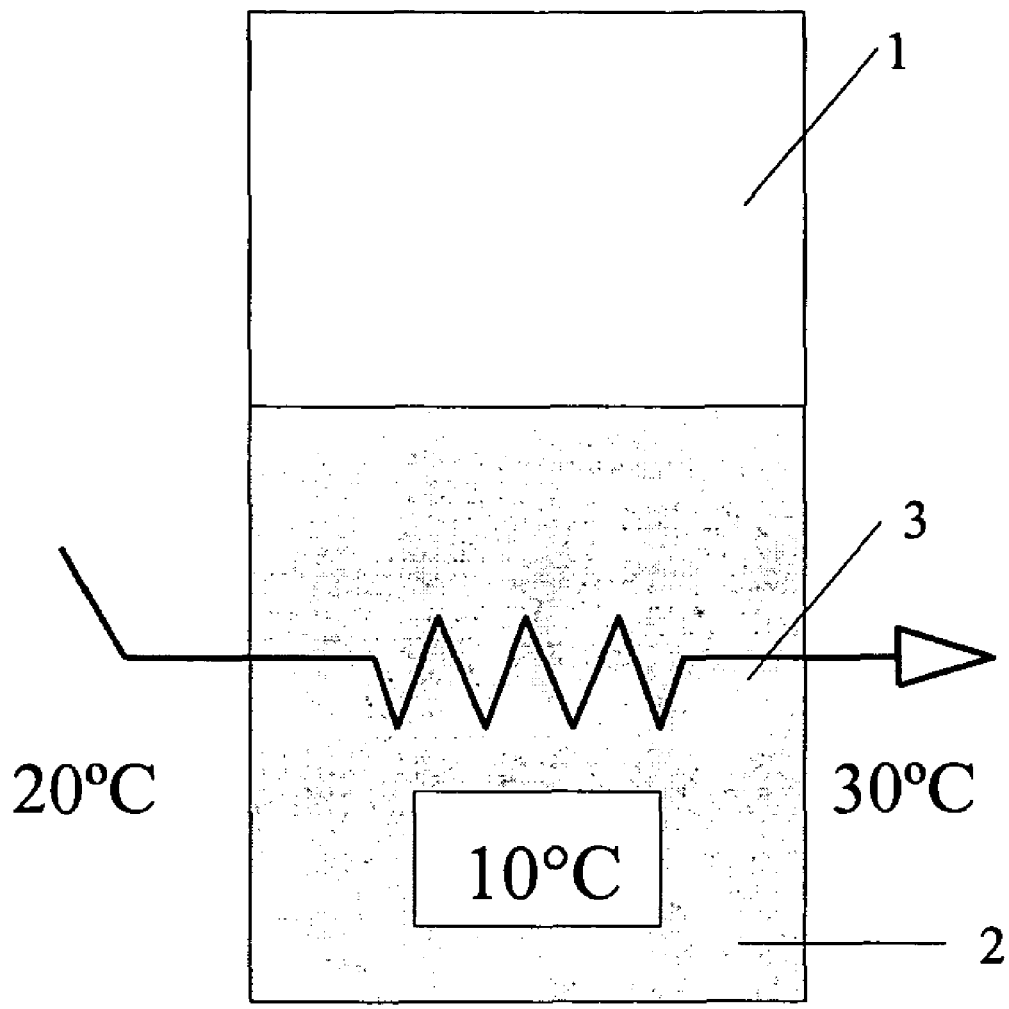
FIG. 1 is a schematic illustration of a reactor containing a process fluid and a cooling coil which is three meters long.
Figure 2:
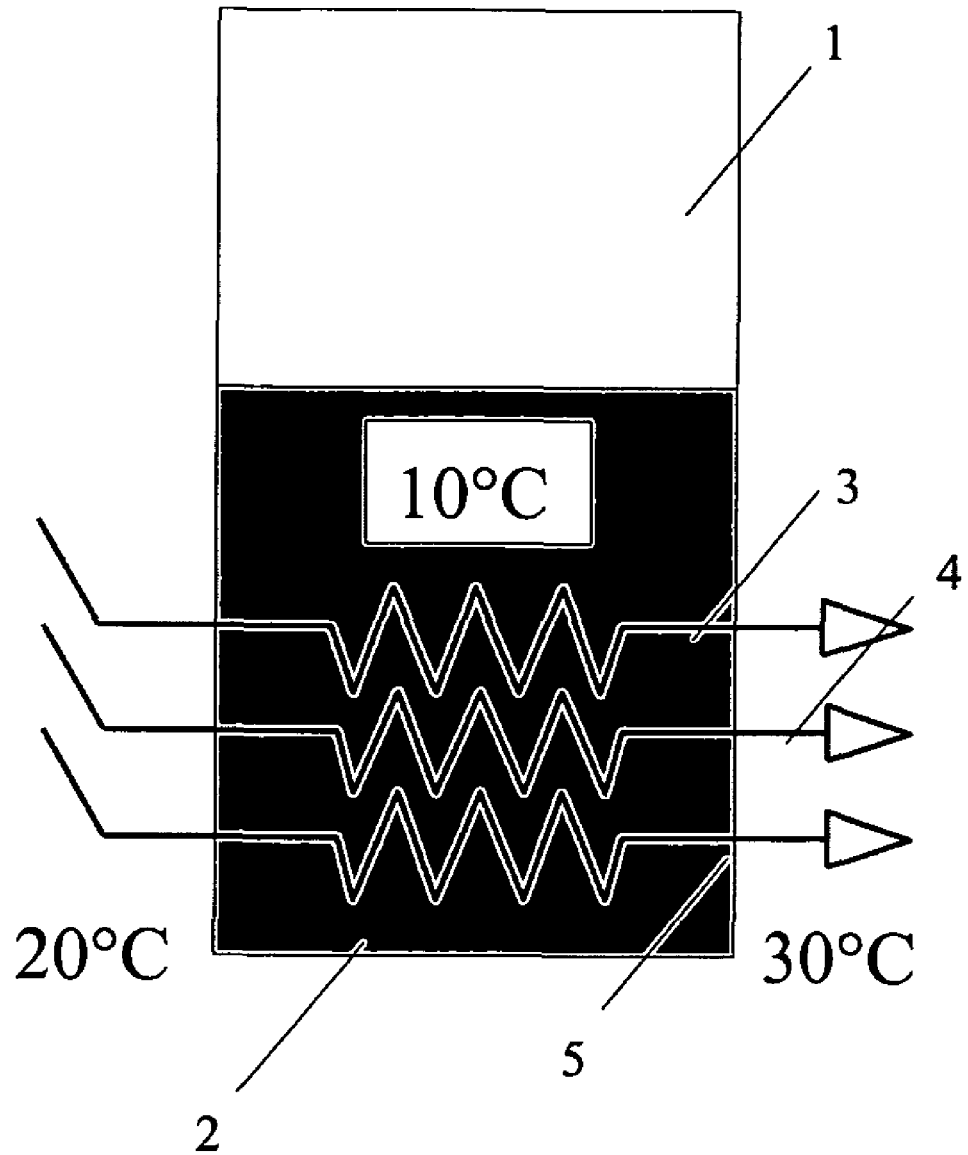
FIG. 2 is a schematic illustration of a reactor according to the present invention having three cooling coils.

The reaction system of the present invention is described with reference to the accompanying drawings in which FIG. 1 is a schematic illustration of a reaction vessel served with a single heat transfer coil (of specified diameter). FIG. 2 is a schematic illustration of a comparable reactor served with three heat transfer coils to provide variable heat transfer area according to the invention.

FIG. 1 is a schematic illustration of a reactor (1) containing a process fluid (2) and a cooling coil (3) which is three meters long. This system is capable of accurately measuring energy changes of between 72 and 260 watts. Measuring energy release rates of less than 72 watts is achieved at the expense of lower accuracy (smaller temperature rise in the heat transfer fluid) or slower control response (slower velocity of heat transfer fluid). Measuring energy release rates of greater than 260 watts, introduces the risk of freezing (or burning/boiling where heat was being applied) as very cold (or hot) heat transfer fluid has to be supplied. The alternative of higher heat transfer fluid flow delivers only moderate improvements (slightly improved U value and higher temperature difference between process and service fluids) in terms of heat transfer capacity and is achieved at the expense of progressively lower accuracy (smaller temperature rise in the heat transfer fluid).

The reactor in FIG. 2 shows how an improved measuring range of 72 to 780 watts can be achieved according to the invention. The versatility has been increased by adding two more coils (4) and (5). When one coil is operating heat generation in the range of 72 to 260 watts can be measured (as in the reactor of FIG. 1). With all three coils operating (at a nominal maximum flow) up to 780 watts can be measured. By this method, it is possible to design a reactor with a wider operating range.

In normal operation, the flow of heat transfer fluid to a coil (or set of coils) will be increased using a flow control valve. When a new coil switches in to accommodate a rising load, the control valve will regulate the flow to ensure smooth transition to the higher flow. This will require a rapid flow control response to the step change in the system pressure drop. To provide a smooth transition between operating conditions and a wide operating range a large number of coils are desirable. It should be noted that the performance of the heat exchanger is best served by having constant flow and temperature (of the heat transfer fluid) to the open conduits. Therefore, where flow control is employed, it is better to limit this to the newly opening coils and to maintain constant flow and temperature to any other coils in operation. Assuming sufficient conduits are employed, the alternative solution is one on/off control (rather than flow control) for the leading coil. Alternatively the opening coil can fluctuate between the open and closed position.

In terms of calorimetry stable conditions in the open coils gives reduced interference due to overshoot effects. In terms of control, maintaining coils at constant temperature permits a much higher correcting temperature on a newly opened coil and this leads to reduced overshoot and is therefore faster and more accurate.

Instrumentation is a key aspect of successful operation of the systems of the present invention. Accurate and sensitive instrumentation must be used for measuring temperatures, the rate of flow of the heat transfer fluid and increasing or reducing the heat transfer area. Instruments must operate over a wide range of flows and this may be achieved by breaking up the coil system into separate modules operated by manifolds. This enables different coils to be brought into or out of operation according to the needs of the system.

Fast and accurate temperature measurements is a key performance requirement. To achieve this, the temperature element is conveniently mounted in fast flowing heat transfer fluid. A minimum hold up volume (of service liquid) should exist between the temperature elements and the heat transfer surface. This is achieved by using sub manifolds on the discharge pipes as shown in FIG. 3.

Figure 3:
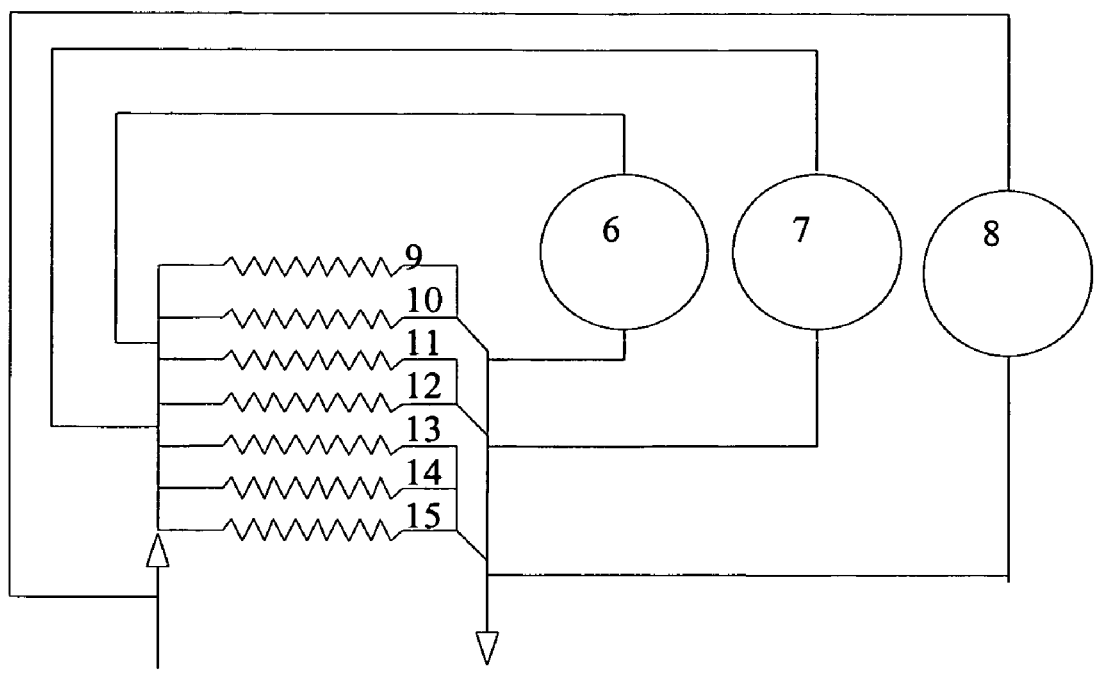
FIG. 3 is a schematic illustration showing three differential temperature measuring devices on a seven-coil system based on coils.

FIG. 3 is a schematic illustration showing three differential temperature measuring devices (6), (7) and (8) on a seven-coil system based on coils (9) to (15). These devices measure temperature change of heat transfer fluid flowing across the coils. The temperature devices work in a cascade fashion. At low flow (coil 9 or coils 9 and 10 operating) measuring device (6) is used for measuring discharge temperature. When three or more coils are operating, measuring device (6) switches to idle and measuring device (7) takes over. When five or more coils are operating, both (6) and (7) switch to idle and measuring device (8) takes over. This concept is applied irrespective of the number of coils and temperature devices used. It is preferred that the linear velocity of the heat transfer fluid as it passes the temperature element is one meter per second or greater (although slower velocities can be tolerated). The temperature devices must be highly accurate and sensitive. It should be noted that separate inlet and outlet temperature devices could be used as an alternative to the differential devices.

In a preferred process, in addition to the normal process temperature transmitters, which constantly measure the process across its entire range and provide the necessary safety interlocks, a second pair of temperature elements can be provided to monitor the specific process set point. This arrangement uses two different types of measuring elements. The main device is preferably an RTD, a 4 wire Pt100 RTD to $1/10^{th}$ DIN standard being especially suitable. The transmitter used to provide the 4-20 mA output signal is spanned to the minimum allowable for the transmitter (similarly any output signal type or temperature span could be used). The temperature transmitter will be calibrated specifically at the process set point. Larger ranges will still give acceptable results, but reducing the span to the minimum possible offers improved accuracy and resolution. Thus this arrangement will provide an extremely accurate means of process temperature measurement.

The element of the temperature measurement system is the part of the device which is in contact with the liquid. In the case of an RTD, its resistance will change in response to changing temperature. The response of an RTD is not linear. The transmitter is the calibrated part of a measuring device and is used to linearise the output to the control system and convert the signal to an industry standard, usually 4-20 mA, but it could also be 1-5 V or 0-10V. A thermocouple's response to a change in temperature is a varying voltage. Usually milli volts per ° C. A thermocouple transmitter will again convert this signal to an industry standard, again more often than not, 4-20 mA. Accordingly the term 'element' is used when describing a physical presence in the process, e.g., a temperature element is located in the reactor and measures the temperature of the reactor contents. The term 'transmitter' when describing aspects of temperature measurement relating to the control system, e.g., a temperature transmitter is calibrated 0-100 ° C. and displays the contents temperature of the reactor.

The limitation of any RTD is its speed of response to a step change in temperature. Typically it can take up to four or five seconds for an RTD to measure a change in temperature. Thermocouples, on the other hand, can respond much more rapidly to temperature fluctuations. For this reason a thermocouple is also used to monitor the process set point, a T type thermocouple being especially suited. Its transmitter will be similarly ranged to the RTD. However, as a T type thermocouple has an accuracy of only + or −1° C., it will not be used to monitor the process temperature. Its function is to monitor the rate of change of the process temperature.

The combined use of these two different types of sensing elements provides a temperature control system, which is both extremely accurate and responsive. It should be noted that not all process operations require this level of temperature measurement accuracy and control. In such cases, more basic temperature control and measurement systems will prove tolerable.

In order to fully utilise this two-element approach, custom software is preferably used to determine which process variable (temperature, or rate of change of temperature) is the most significant at any one instance in time. Other temperature measuring devices such as optical (e.g. Infra Red) may be used. Speed of measurement is important for effective operation of the system.

Figure 4:
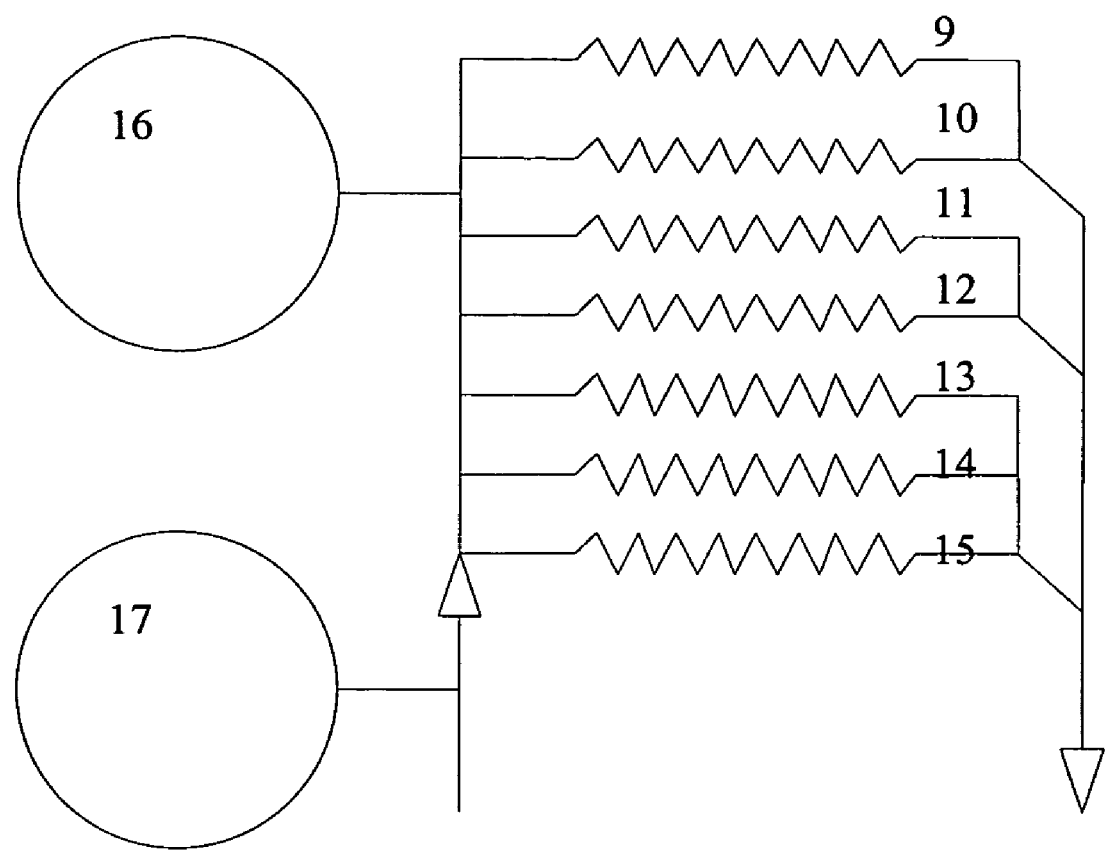
FIG. 4 depicts a flow measurement system for the reactor according to FIG. 3 employing multiple flow devices.

Accurate measurement of flow is also important for effective operation. FIG. 4 shows a flow measurement system for the reactor shown in FIG. 3 employing multiple flow devices. Flow device (16) is a low range device for measuring flow when coils (9) or coils (9) and (10) are in operation. When three or more coils are in operation, flow device (17) takes over and (16) switches to idle. Any number of flow transmitters can be used to achieve satisfactory accuracy. As a general rule, the number of flow devices to be used should be calculated as follows number of flow devices=$(F_{max}-F_{min})/(R \cdot F_{min})$ where
$F_{max}$=maximum flow (kg·s$^{-1}$)
$F_{min}$=minimum flow (kg·s$^{-1}$)
R=turn down ratio of the flow instrument The above equation makes reference to mass flow. The equipment can use a volume flow device however provided the system converts volume flow data into mass flow data. This can be done automatically by the control software (mass flow=volume flow×liquid density). For sensitive systems (or those with a wide temperature range) compensation should be made for changes in liquid density. Information on liquid density can be input manually into the control system. Alternatively, the control software can calculate the density based on temperature using established mathematical relationships. Alternatively a mass flow device may be used.

In the present invention, the reactor is operated at constant temperature. Any losses or gains in temperature to the environment will be recorded as reaction activity. It is preferred that the system be such that there is no direct heat transfer between the conduits. Where the conduits pass through the process fluid the process fluid itself may provide sufficient insulation to prevent direct heat transfer between the conduits. If however the conduits are or form part of the vessel wall it may be necessary to provide insulation between the conduits.

In our preferred system three measures are used to take any heat losses into account.

Heat losses are compensated for by zero calibration prior to reaction

The vessel is lagged or located in a box to minimise heat loss

Figure 5:
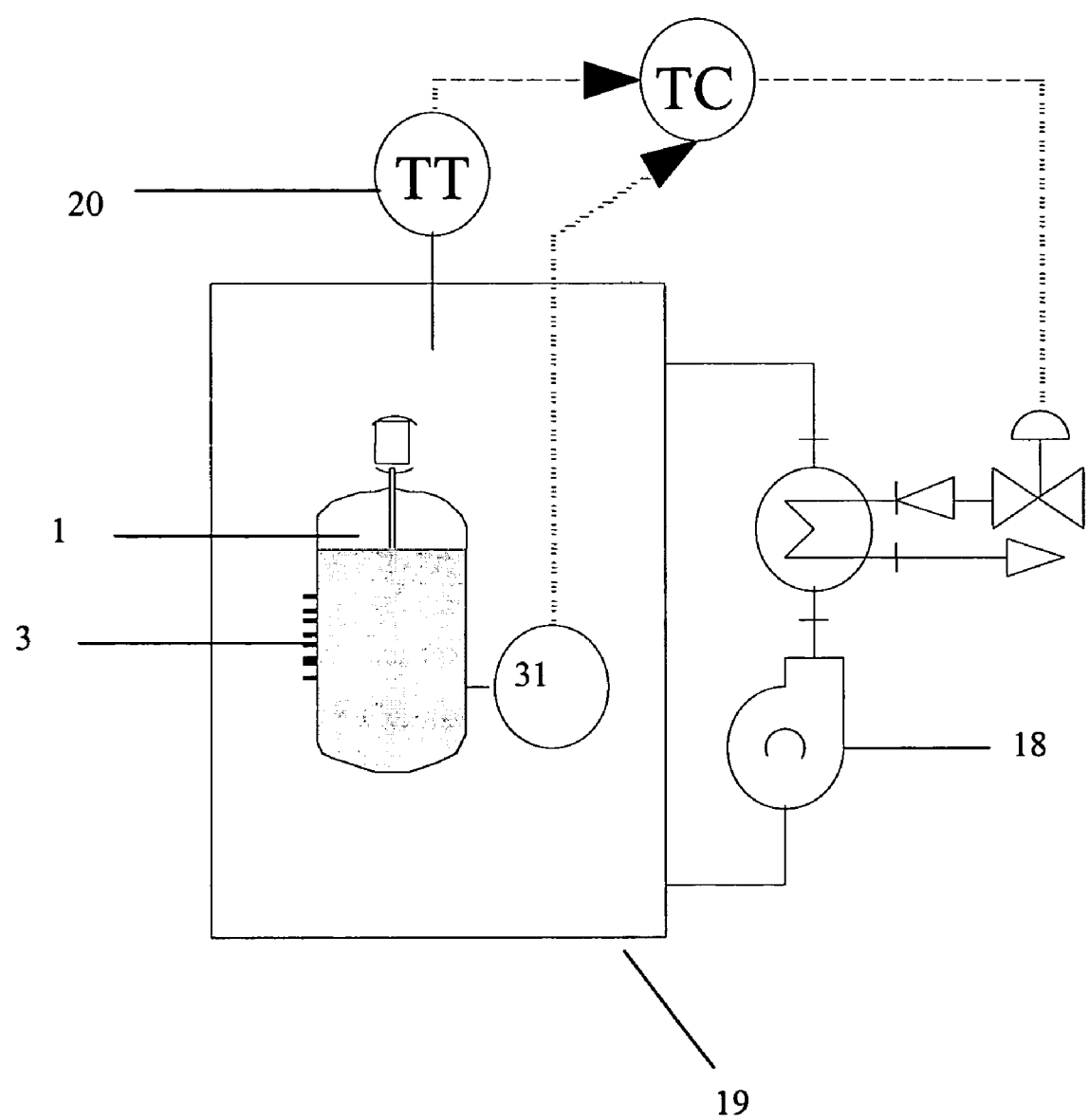
FIG. 5 is a schematic representation of a system according to the present invention having a second heating cooling loop with a fan circulating air within the temperature box.

For very sensitive systems the insulating box is temperature controlled by an independent loop as shown in FIG. 5.

The arrangement in FIG. 5 shows a second heating cooling loop with a fan (18) circulating air within the temperature-controlled box (19). The air temperature within the insulated box is determined by temperature measurement device (20) and is maintained at the process reaction temperature (31). This eliminates heat loss/gain to/from the environment.

Any net heat flows in and out of the system must be monitored or controlled. Where liquids (or dry gases) enter or leave the system, these should be at reaction temperature. If not they should be of known specific heat and monitored for temperature and flow. Vapour carried out of the system presents a greater problem. If the gas flow is significant, two options can be employed. Heat losses with off gas are measured in trial runs and compensated for in the calculations. This solution has to be used with care for batch operation when gas evolution varies with time. Accordingly for batch operation it is preferred that the gas flow out of the reactor be measured and the information translated into heat flow data.

The system works most effectively under isothermal conditions. It can however be used for reactions where the process temperature changes. In this case it is necessary to measure the heat capacity of the system as follows:

$$\Sigma M \cdot Cp = (M_p \cdot Cp_p) + (M_c \cdot Cp_c)$$

where

ΣM·Cp=heat capacity of the system (kJ/° C.)
$M_p$·=mass of process fluid (kg)
$Cp_p$=specific heat of process fluid (kJ·kg$^{-1}$K$^{-1}$)
$M_c$·=mass of equipment in contact with process fluid (kg)
$Cp_c$=specific heat of equipment in contact with process fluid (kJ·kg$^{-1}$K$^{-1}$)

In practice ΣM·Cp may be calculated by using the reactor. This is achieved by heating or cooling the process fluid and measuring heat lost or gained over a given temperature change when no heat is being absorbed or liberated by the process.

$$\Sigma M \cdot Cp = Q/(t_s - t_f) \ (kJ/° C.)$$

where

ΣM·Cp=specific heat of the system (kW/° C.)
Q=measured quantity of heat added or removed (kJ)
$t_s$=temperature at the start of heating or cooling (° C.)
$t_f$=temperature at the finish of heating or cooling (° C.)

This heat capacity information may be fed into the system and used as a correction factor when the temperature changes during the process. The heat capacity information also serves as useful process data.

Conventional reactors have fixed area heat transfer surfaces (or occasionally several elements such as separate sections on the bottom dish and walls). They perform most effectively with a high and constant flow rate of heat transfer fluid to the jacket (or coils). Process temperature is controlled by varying the heat transfer fluid temperature. In the preferred system of the present invention, the area of the heat transfer surface may be varied according to the needs of the reaction (although some variation in heat transfer fluid temperature can also be used).

Figure 6:
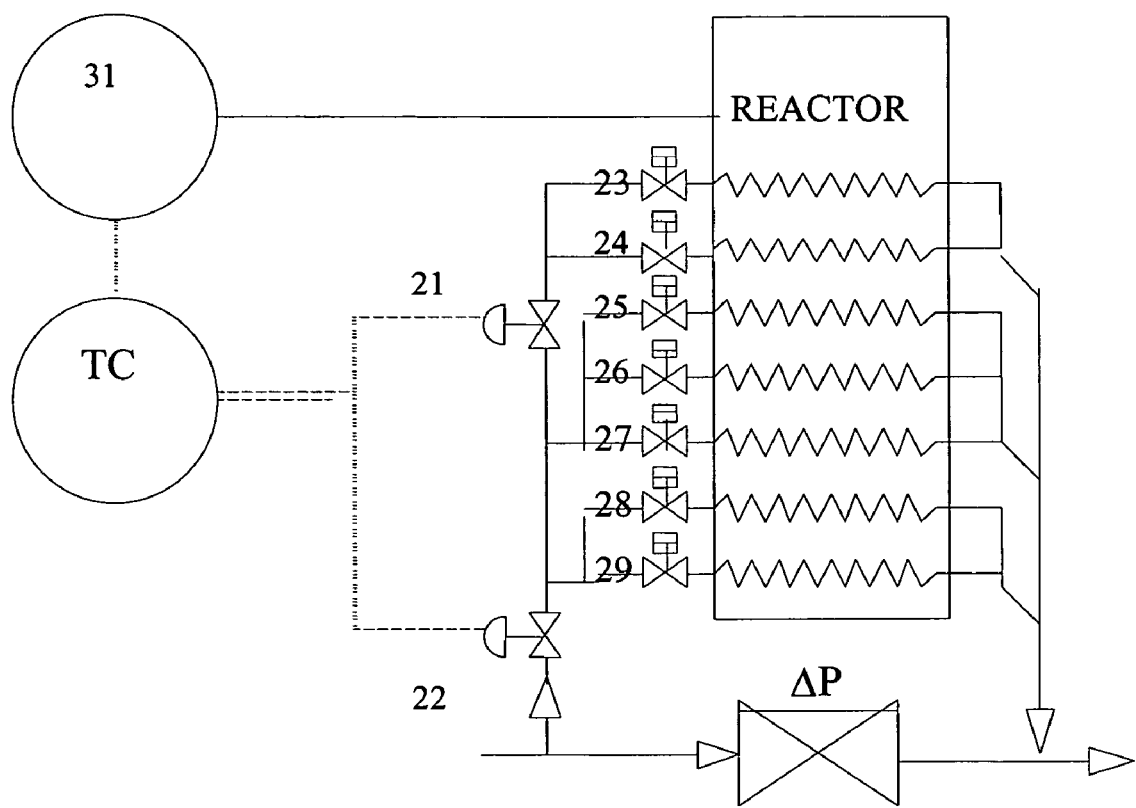
FIG. 6 is a schematic representation of a control arrangement for control of the heat transfer fluid using a variable area heat transfer surface.

A typical control arrangement for control of the heat transfer fluid using a variable area heat transfer surface is shown in FIG. 6. In FIG. 6 valves (21) and (22) are control valves that regulate flow of heat transfer fluid to the heat transfer coils. The extent to which they are open is determined by a temperature output measure from the reactor (or vessel). With the process at idle, valve (23) is open and sufficient flow permitted to compensate for heat gain from the agitator. As load is applied to the process, valve (21) opens to permit the flow of more heat transfer fluid. When valve (21) is open beyond a pre-set point (or when flow rate dictates) valve (24) will open and valve (21) will close up slightly to compensate. As valve (21) approaches the top of its control range, valve (22) takes over. As valve (22) progressively opens the valves (23) to (29) are opened in a cascade fashion. In a preferred operation greater constancy of the velocity of the heat transfer fluid with the open coils is achieved by once a value is open it remains open and modulation of the flow is limited to the next coil to be brought into operation.

The required number of flow control valves can be calculated in the same manner as for flow devices (see above).

Any number of control valves can be used and they can be installed in series (as shown) or in parallel. In this preferred system the extent to which valve (21) and (22) are open is dictated by the process load. The number of on/off valves (which turn the coils on and off) open is dictated either by the position of the control valves or the measured flow.

The disadvantage with using flow control valves as described above is that they cause undesirable fluctuations in heat flow from an external source. A preferred alternative to this is a large supply manifold held at constant pressure. This ensures that the open coils always see heat transfer fluid at constant flow and temperature. In this case, only the newly opening coils are subject to flow control (by flow regulations or on/off control). A further improvement of this control system is the subject of United Kingdom Patent Application 0121375.0.

The heat transfer fluid is applied to the control equipment at constant pressure and temperature. In some cases temperature can also be varied where it is necessary to increase the operating range.

A key requirement of this invention is reliability. This is particularly important in pharmaceutical applications where current good manufacturing practice (cGMP) dictates that the equipment operates within stated design parameters.

To provide a means of calibration and as a performance check, the reactor may be fitted with an electrical heater (or some other type of reference heater). By supplying a measured current to the heater, reliable reference loads are provided for calibrating the system and checking performance. In pharmaceutical applications, control and data acquisition systems together with software should be validated to comply with cGMP standards.

Figure 9:
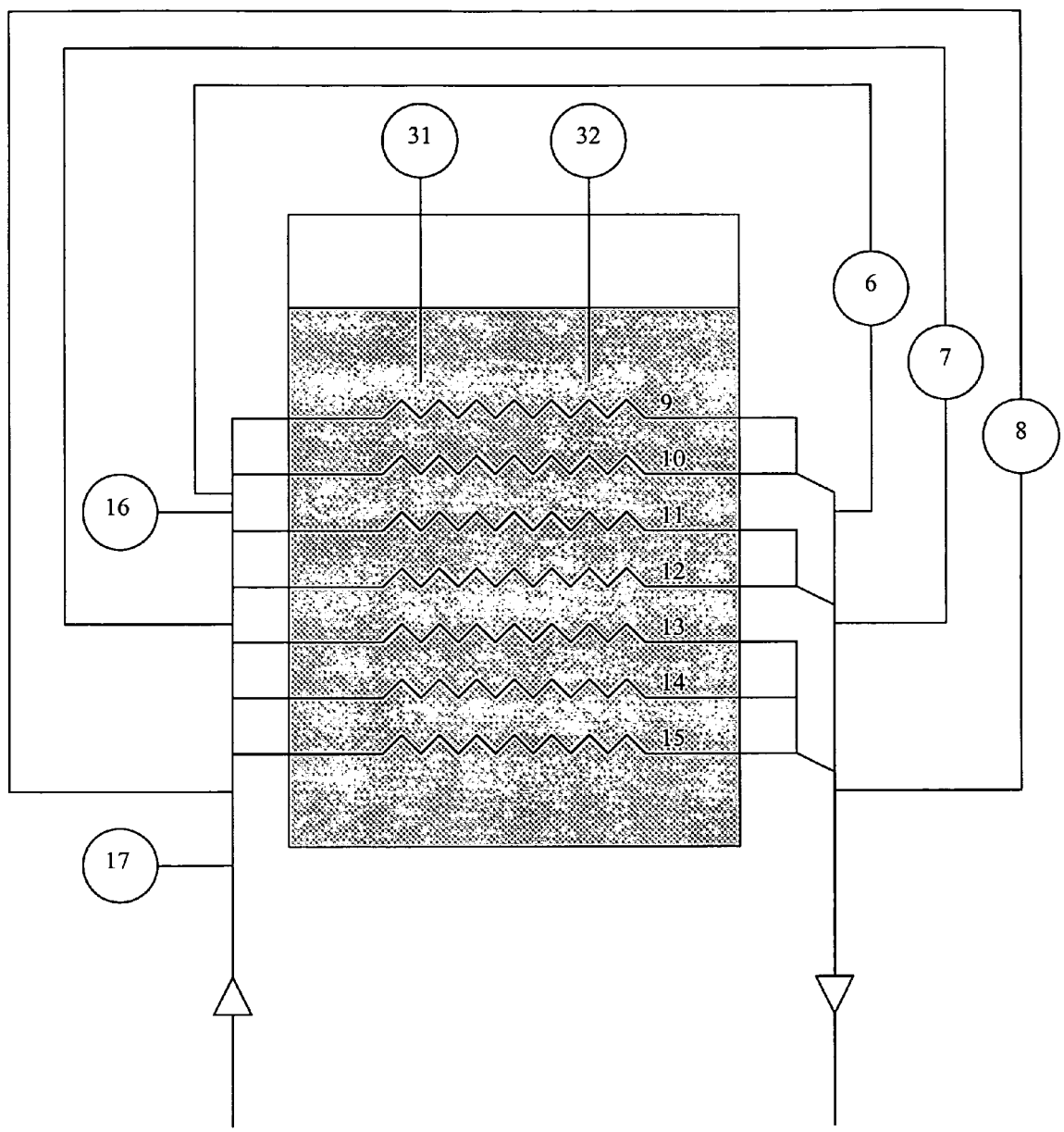
FIG. 9 is a schematic illustration of the process instrumentation according to the present invention.

The equipment incorporates both conventional instrumentation and process specific instrumentation. These process specific instruments operate at a higher than normal accuracy when compared to conventional instrumentation. FIG. 9 is a schematic illustration of typical process instrumentation which consists of:

a process temperature RTD instrument (31)
a process temperature thermocouple instrument (32)
heat transfer fluid differential temperature instruments (6), (7) and (8)
heat transfer fluid flow meter instruments (16) and (17)

For the process temperature RTD instrument (31) and the heat transfer fluid differential temperature instruments (6), (7) and (8), matching the RTD sensor to the temperature transmitter can result in significant improvements. The specific characteristic of an RTD sensor is unique to each device. By storing this information in the transmitter improvements in accuracy are obtained. The constants used in this technique are known as the Callendar-Van Dusen (CVD) constants. The present invention is unique in that it uses additional calibration steps to enhance the accuracy of its instrumentation. For example, if the CVD technique is coupled with the use of high accuracy RTDs (typically class B to $\frac{1}{10}^{th}$ DIN standard) process specific calibration may then be carried out to bring about further improvements in accuracy.

By 'process specific calibration', (e.g. the optimum reaction temperature) we mean that the instrument is calibrated specifically at the normal process set point of an instrument and that the measuring system error is adjusted, such that at this operating point best accuracy is achieved (for a normally calibrated instrument, best accuracy is usually given at the maximum calibrated range, or at a point dictated by the characteristics of the sensor). For example if a process is to be controlled at 35° C., instrument (31) would be calibrated across a small range, say 25 to 45° C. Furthermore, the instruments would be calibrated at 35° C. and adjusted so that at this specific point the error of the measuring system is the minimum achievable. Once installed and connected to the control system, the calibration of the instrument loop can be verified as a complete installation and any control system errors compensated for. The control system hardware is designed to minimise errors (precision components must be used) and thus optimise accuracy. Similarly the instrumentation installation must be such as to minimise measuring error. The use of these additional steps, will allow maximum possible calibration accuracy to be obtained.

The process temperature thermocouple (32) will be calibrated in a similar manner, but as it is used to measure rate of change of temperature as opposed to temperature, its overall accuracy, although still important, is less significant. Where high accuracy thermocouples are available they may be used as the primary measuring element.

The heat transfer fluid differential temperature measuring instruments (6), (7) and (8) will also employ this same technique to ensure best calibration accuracy is achieved.

For the heat transfer fluid flow instruments (16) and (17) the technique is again similar. Calibration in this instance is carried out over a small operating range with the emphasis on achieving the best accuracy at the preferred flow. By using multiple instruments calibrated over relatively small operating ranges, e.g. 0-1, 1-2, 2-3 etc., a significant improvement in accuracy is achieved than by using a single instrument calibrated over the range 0-3. Best accuracy is achieved by using a suitably sized instrument with a normal flow of 80 to 90% of the instrument span. Again, once installed in the field and connected to the control system, the calibration of the instrument loop should be verified as a complete installation and any control system errors compensated for. The control system hardware is again designed to minimise errors and thus optimise accuracy.

Routine calibration of the heat measuring equipment may be carried out in several steps as follows:

The first step is zero calibration. For accurate operation, zero calibration should be carried out for each type of process used. This permits the control system to compensate for any 'non-process' energy changes (e.g. heat gains and losses to the environment, energy gain from the agitator etc). The vessel is filled with liquid and the agitator switched on. It is then heated to the reaction temperature. When the temperature is stable at the operating temperature, the heating/cooling system will function at a very low level to compensate for non-process energy changes. The control system is zeroed under these conditions.

The second stage is to range and span the system. This is carried out by heating or cooling with a reference heater or cooler. This may be in the form of an electrical heater or an independent heating/cooling coil. Heating (or cooling) is carried out at several different energy input levels to range and span the system.

Alternatively the instruments may be tested individually in which case the second step of the above process may not be necessary.

We have found that the reactor systems of the present invention are extremely useful as batch chemical synthesis reactors. We have also found that the invention enables the same size of machine to be employed for development, pilot plant and full manufacturing purposes.

Figure 7:
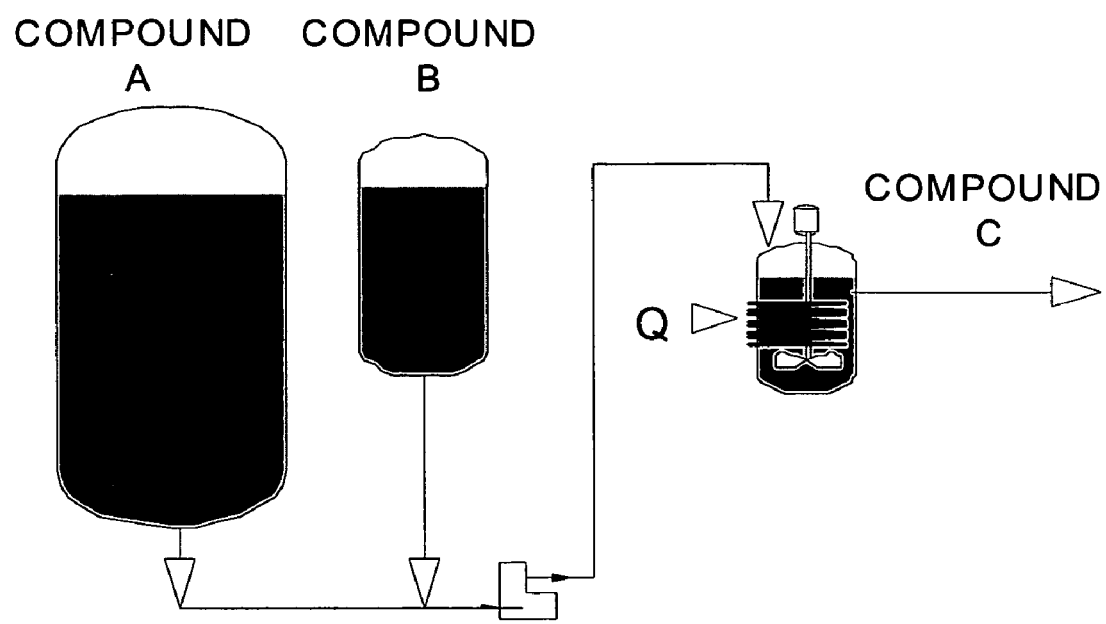
FIG. 7 is a schematic illustration of use of the heat transfer reactor according to the present invention in a batch flow process.

The variable area heat transfer reactor of this invention is ideal for fast exothermic reactions, where it can operate as a small continuous flow reactor on processes hitherto conducted as batch reactions. Unlike large conventional batch reactors, it is possible to operate in this mode as the reaction is continuously monitored. Any fall off in conversion efficiency is detected immediately and forward flow is stopped. The arrangement for this system is shown in FIG. 7. Alternatively the vessel shown in FIG. 7 might be a heat exchanger (without agitator) where turbulence is achieved by restricting the hydraulic path of the process fluid. The benefits of operating in this mode are various. The capital cost of a reactor for this type of application is substantially lower than a conventional reactor. In addition higher throughputs can be achieved. This type of equipment is also ideal for dangerous reactions as the inventory of reactants can be much smaller than that needed for conventional reactors. The equipment can also be programmed to stop reagent addition if unconsumed reactant starts to accumulate.

Figure 10:
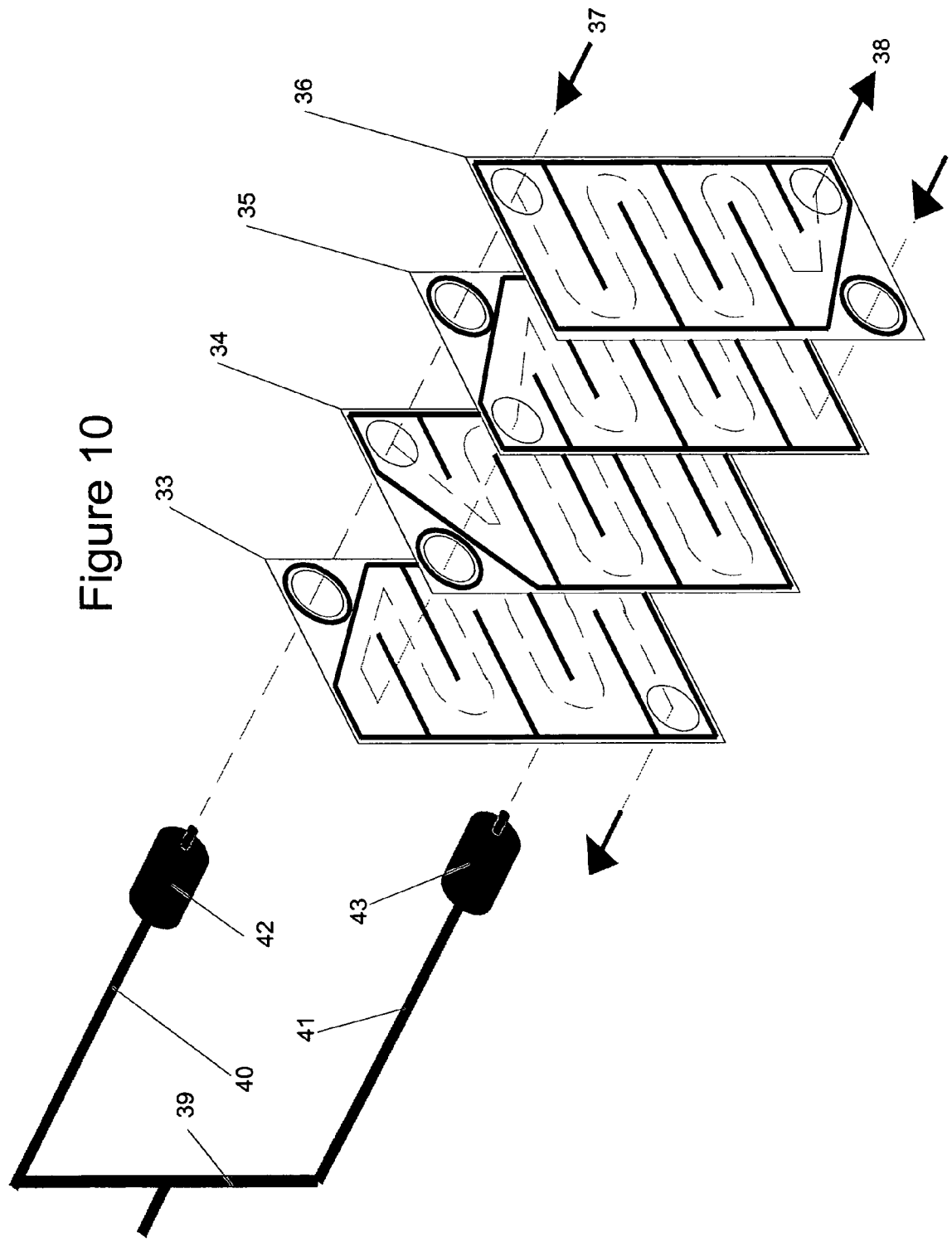
FIG. 10 is a schematic exploded illustration of a plate heat exchanger according to the present invention.
Figure 11:
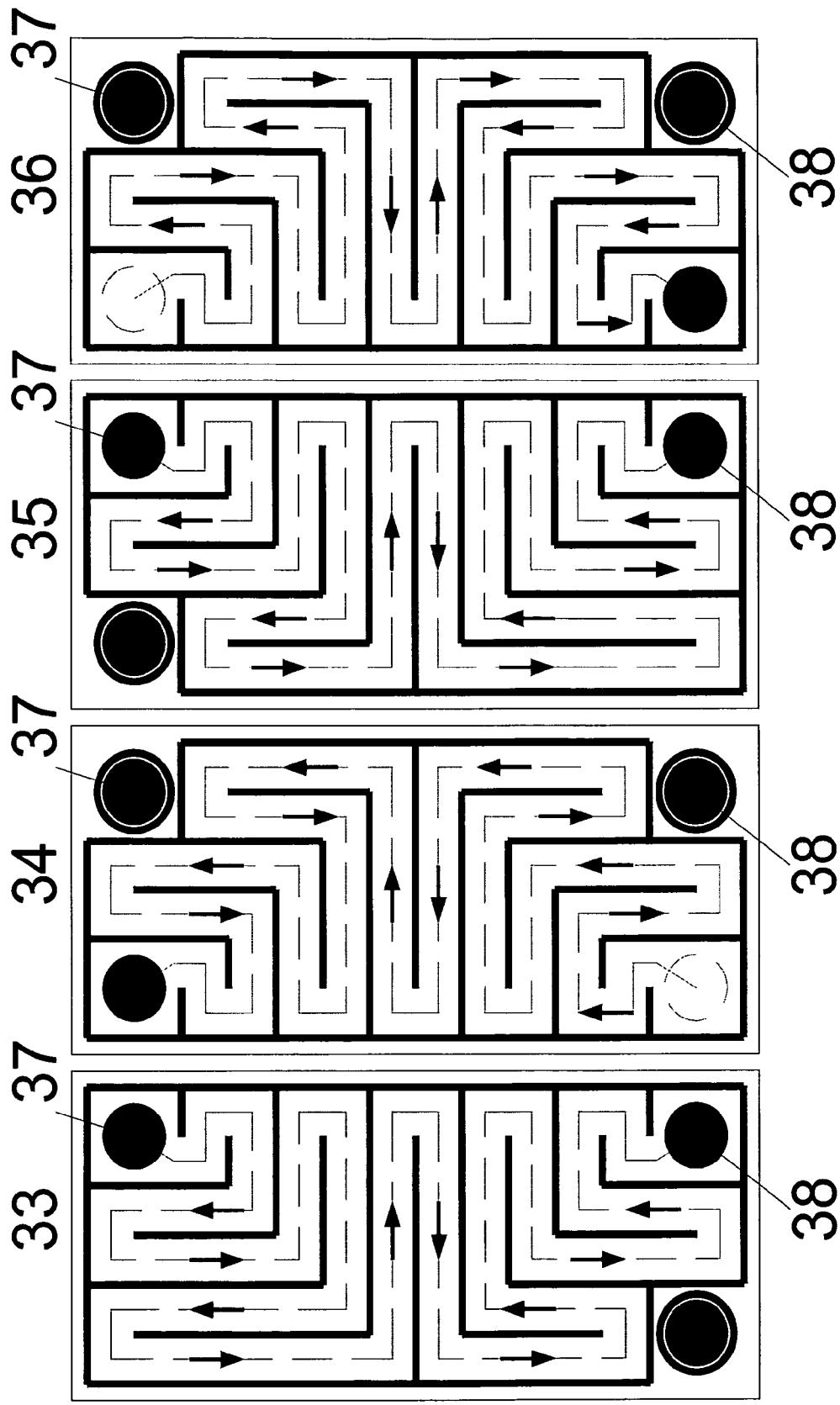
FIG. 11 depicts the flow of heat transfer fluid through the plates of the plate heat exchanger of FIG. 10.
Figure 12:
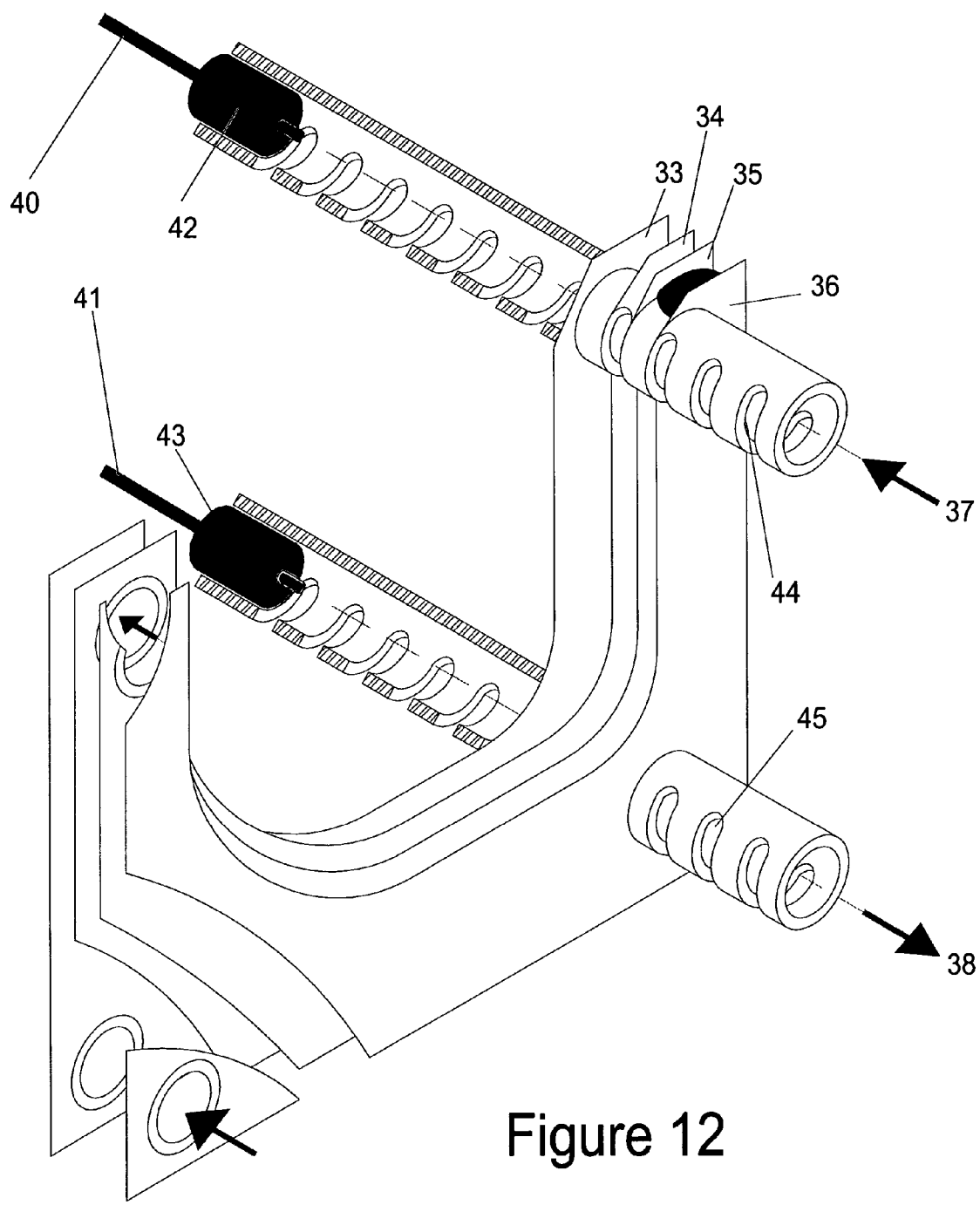
FIG. 12 depicts a valve system used to control the flow of the heat transfer fluid to the various plates which make up the plate heater.

FIG. 10 is a schematic exploded illustration of a plate heat exchanger which may be used in the present invention. FIG. 11 shows the flow of heat transfer fluid through the Plates (33), (34), (35) and (36) of plate heat exchanger of FIG. 10 and FIG. 12 shows a valve system which can be used to control the flow of the heat transfer fluid to the various plates which make up the plate heater.

A plate heater exchanger is generally made of several closely associated parallel plates and FIG. 10 shows four such plates (33), (34), (35) and (36) exploded away from each other to show the fluid flow paths available within the plates. According to the present invention the plates are provided with tubes (37) and (38) provided with openings which can be opened or closed to allow or prevent heat transfer fluid from entering a particular plate. A valve system (39), (40), (41), (42) and (43) is provided which contains plungers (42) and (43) so that the valve system can slide back and forth along tubes (37) and (38) thus opening and/or closing the entrances to the individual plates. In this way the valve system may be moved according to the determination of the heat generated or consumed by the reaction to provide temperature control according to the present invention.

Figure 13:
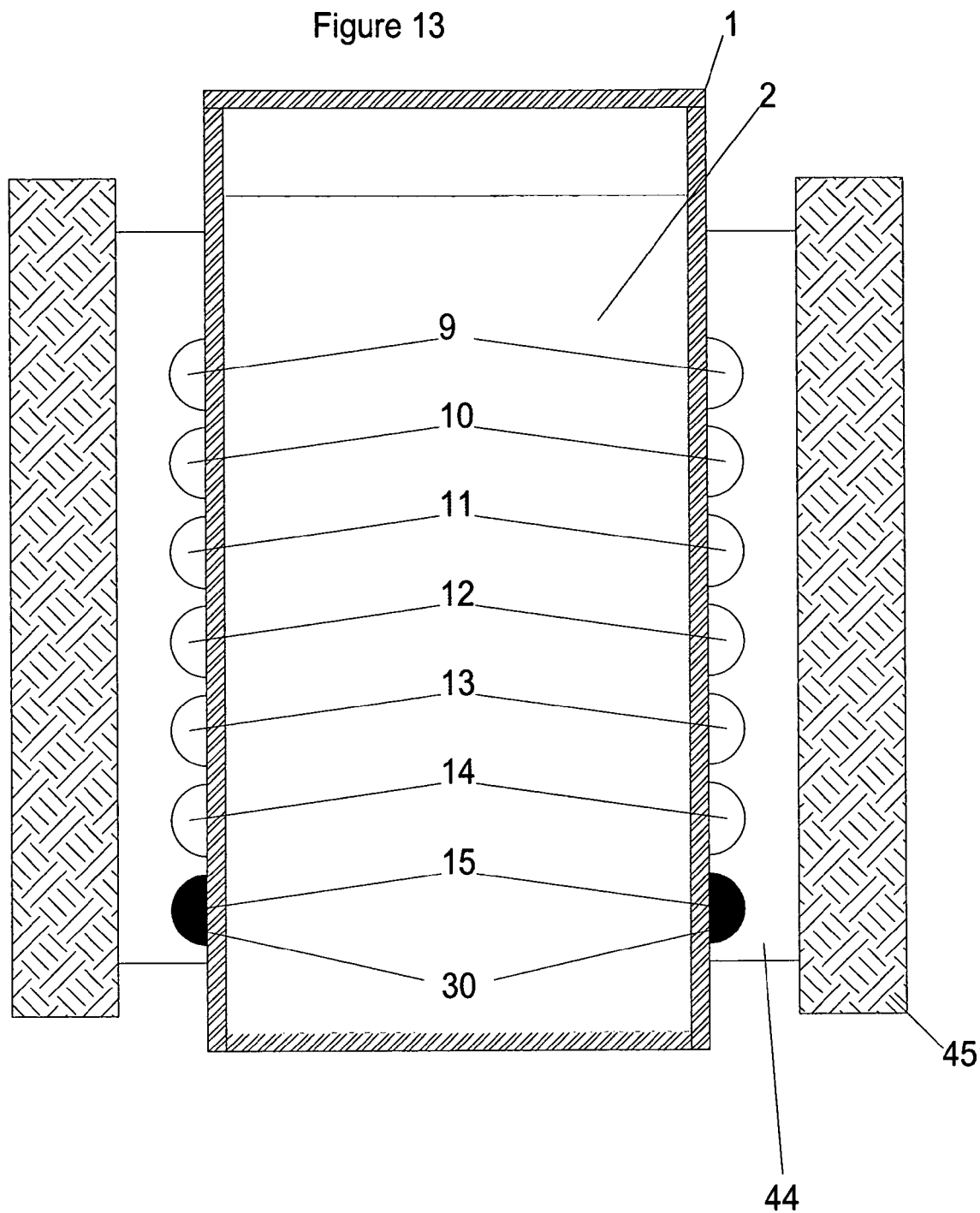
FIG. 13 depicts an alternative system in which the conduits form part of the wall of the reactor vessel.

FIG. 13 shows an alternative system in which the conduits (9), (10), (11), (12), (13), (14), and (15) form part of the wall of vessel (1). As with FIG. 2, (2) is the process fluid and (30) is the heat transfer fluid. The conduits may be formed in a single moulded sheet (44) in which spurs are formed between the conduits to prevent heat transfer between conduits. The reactor is also provided with an external insulation jacket (45). The temperature change of the heat transfer fluid across the reaction may be measured by the techniques previously described and the information used to bring the conduits into and out of operation as described for the reaction system of FIGS. 2 to 6.

The invention is useful in slow exothermic reactions including reactions where large liquid volumes are held. In these reactors the data is obtained, analysed and used in a manner similar to the continuous reactor described above. The benefits of using this equipment for slow reactions is that the addition rate of the components can be regulated to prevent accumulation of unreacted chemicals. It is also possible to identify the end point of the reaction which offers substantial savings in plant utilisation as the product can be transferred forward with the confidence that it satisfies a key quality control objective. In some cases, accurate identification of end point also enhances product quality and yield. The invention also enables energy efficiencies and better reaction yields with less waste of reactants.

The rate at which heat can be transferred between the process fluid and the heat transfer fluid is dictated (in part) by the overall heat transfer coefficient (U). The larger the value of U, the smaller the heat transfer area required. The U value may be calculated from three components.

The heat transfer resistance through the process fluid boundary layer.
The heat transfer resistance through the coil wall.
The heat transfer resistance through the heat transfer fluid boundary layer.

The boundary layers are the stagnant layers of liquid either side of the conduit, preferably coil, wall. The faster the agitation (or liquid flow), the thinner the boundary layer. Thus high flow rates give better heat transfer. Also liquids with good thermal conductivity give better heat transfer through the boundary layers.

Heat transfer mechanism across the conduit, preferably coil, and wall is similar, except (unlike the boundary layers) the distance through which the heat has to conduct is fixed. Higher heat transfer rates are achieved where the coil material has high thermal conductivity. Higher heat transfer rates are also achieved where the coil material is thin.

Thus a high U value requires both a thin conduit, preferably coil, material (with high thermal conductivity) and turbulent conditions in both liquids (the more turbulent, the better). The higher the U value, the smaller the area required for heat transfer. This means a shorter heat transfer coil.

It is therefore preferred to use the thinnest walled conduits, preferably coils, possible without compromising mechanical strength and corrosion tolerance. A typical wall thickness would be ½ to 4 mm.

The material from which the conduit, preferably coil, is fabricated is not critical but should be inert to the process fluid. Preferred materials include, stainless steel for non-corrosive organic fluids, Hastelloy C (22 or 276) or similar alloys for most reactions using chlorinated solvents or other corrosive compounds. Tantalum and titanium are suitable where special corrosive conditions exist. In some applications other materials such as plastic, glass, glass lined steel or ceramics could be used.

The techniques of the present invention can be used for measuring heat of physical changes such as the heat of crystallisation and evaporation.

The present invention may employ the temperature control means described in our United Kingdom Patent Application 0121375.0 which employs a bank of conduits which are opened and closed to the fluid according to a temperature measuring device in the media whose temperature is to be controlled. The flow of the heat transfer fluid to the conduits may also be controlled by a multi-port flow control valve such as that described in our United Kingdom Patent Application 0121071.5.

In addition the reaction system of the present invention may be calibrated using the techniques described in United Kingdom Patent Application 0110293.8. Control systems which may be used in the reaction system of the present invention are described in United Kingdom Patent Application 0110295.3.

For purposes of illustration only the following examples show the sizing of heat transfer coils.

Example 1 illustrates the sizing of an individual heat transfer coil such as that used in FIG. 1. Examples 2 and 3 illustrate the sizing and use of multiple heat transfer coil systems according to the invention.

In these examples some of the numbers used are arbitrary and are chosen for purposes of illustration only. The examples illustrate the sizing of coils for a batch reactor where an exothermic reaction takes place. In this, a theoretical reaction reagent A is reacted with product B to produce a new compound C as follows.

A+B C where
A=kg of A
B=kg of B
C=kg of C
The heat liberated Hr is as follows:

$$Hr_c = 1,000 \; (kJ/kg_c) \quad (1)$$

The batch reactor is pre-filled with component B. Component A is added slowly (alternatively the two components could be pumped continuously through the reactor in the desired ratios). For the purposes of this example it is assumed that it is a fast reaction and component B reacts immediately on contact with A. The heat liberated is therefore proportional to the rate of addition (of A). If it is assumed that the addition rate is such that 0.001 kg/second of C is produced The heat load of the reactor (q)=0.001×1000=1 kW.

The reaction is also assumed to take place at constant temperature so that the heat load on the cooling fluid is also 1 kW.

Figure 8:
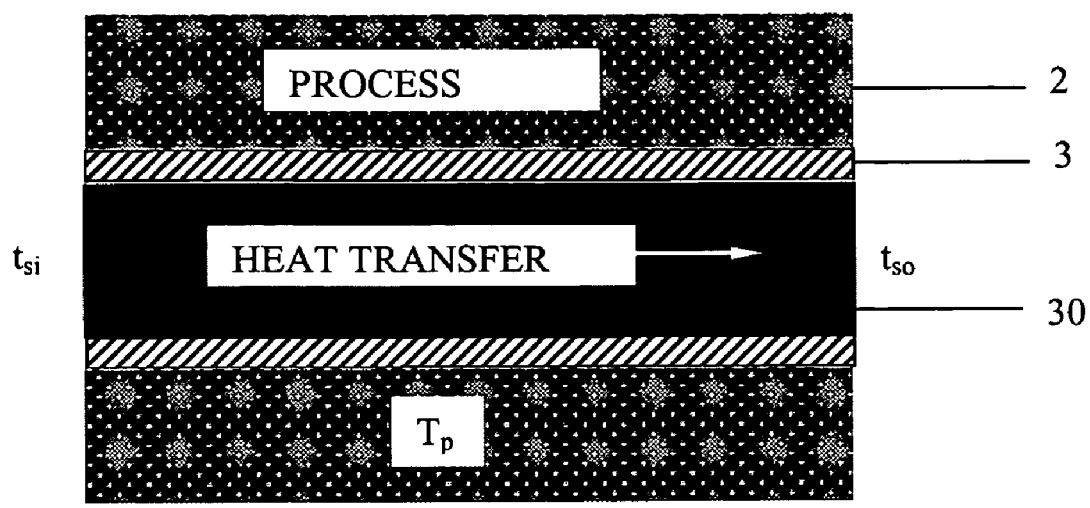
FIG. 8 is an alternative embodiment of a heat exchanger (without agitator) where turbulence is achieved by restricting the hydraulic path of the process fluid.

FIG. 8 is a schematic illustration of a section through a typical heating/cooling coil such as coil (3) of FIG. 1 in the process fluid (2) through which flows the heat transfer fluid (30).

EXAMPLE 1

The heat transfer coil (3) serves two functions, it controls the process temperature and also measures the quantity of heat liberated (or absorbed); for the purpose of this example, the term $t_{si}$ is used for the measured inlet temperature of the heat transfer fluid and $t_{so}$ for the outlet temperature of the heat transfer fluid. For effective operation, two factors need to be satisfied.

i The temperature change in the heat transfer fluid $(t_{si}-t_{so})$ must be sufficiently large to provide a good measurable difference. For this example a 10° C. temperature change of the heat transfer fluid $(t_{si}-t_{so})$ has been selected.

ii In general, the temperature difference between the heat transfer fluid and the process fluid must be as high as possible but not so great that boiling, burning or freezing occur on the pipe surface. Assume that the reaction temperature is 30° C. $(t_p)$. Also assume that the lowest temperature at which service fluid can be delivered to the system is 5° C. (to avoid freezing on the outer surface). Thus the service fluid inlet temperature $(t_{si})$ is 5° C. and the outlet temperature $(t_{so})$ is 15° C. [since $(t_{si}-t_{so})$ is 10° C.].

Once the choice for $(t_{si}-t_{so})$ is made, the mass of the heat transfer fluid can be determined as follows:

$$m = q/Cp(t_{si}-t_{so}) \quad (1)$$

where
m=mass flow of heat transfer fluid (kg/s)
q=heat gain by the heat transfer fluid=1 (kW) (in this example 1 kW is the heat of reaction)
Cp=specific heat of heat transfer fluid=1.6 kJ·kg$^{-1}$·K$^{-1}$ (based on the choice of the synthetic heat transfer fluid)
$t_{si}-t_{so}$=temperature change of heat transfer fluid (selected to be 10° C.)
Thus from equation (1), the mass flow (m)=1/1.6× 10=0.0625 kg/s Assume the density of the heat transfer fluid=840 kg/m$^3$.

Thus the volume flowrate of the fluid (W)=0.0625/840=0.000074 m$^3$/s

Optimising coil geometry and the velocity of the heat transfer fluid is an iterative process. Low velocity of the heat transfer fluid through the heat exchange coil gives rise to poor control and measurement response. Low velocity also results in a large ratio of thermal mass of heat transfer fluid to heat load. This tends to magnify any errors of temperature measurement. High liquid velocity is desirable as it gives faster control response and a better ratio of thermal mass to heat load. As the velocity is increased however, the pressure drop through the coil gets higher.

Accordingly the optimum coil will be long enough to give adequate heat transfer area without incurring an excessive pressure drop. If the diameter is too small, the pressure drop will be too high (due to high liquid velocity and long pipe length). If the diameter is too large, the liquid velocity will be too low.

In this example an initial calculation based on a 4 mm diameter pipe is made for the first iteration as follows:

At a flowrate of 0.000074 m$^3$/s through a 4 mm bore pipe, the pressure drop of the heat transfer fluid is calculated as being 1.24 bar/m (based on synthetic heat transfer fluid).

The pipe length is calculated from the relationship $$L = A/\pi D$$

where
L=pipe length=(m)
A=surface area of pipe (m$^2$)
D=pipe diameter=0.004 (m)
π=3.1416

If the heat exchanger is a plate the parameter equivalent to pipe length is the flow path of the heat transfer fluid though the place and appropriate modifications to the calculation will be required.

The surface area (A) required for control of the reaction is determined from the heat transfer capabilities of the pipe as follows:

$$A = q/U \cdot LMTD \ (m^2)$$

where
A=surface area of pipe (m$^2$)
U=overall heat transfer coefficient=0.730 (kW·m$^{-2}$·K$^{-1}$) (estimate for organic process fluid and synthetic oil heat transfer fluid)
LMTD=[($T_p$−$t_{si}$)−($T_p$−$t_{so}$)]/ln[($T_p$−$t_{si}$)/($T_p$−$t_{so}$)] (° C.) (log mean thermal difference between process and service fluids)
Also
$T_p$=30
$T_{si}$=5
$T_{so}$=15
Thus LMTD=19.6 (° C.)
Therefore A=1/(0.730×19.6)=0.07 m$^2$ (m$^2$)
Therefore L=0.07/(3.1416×0.004)=5.6 (m)
The pressure drop through the line=5.6×1.24=6.9 bar
The linear velocity can also be calculated using the continuity equation as follows:

$$V = W/A$$

where
V=linear velocity (m/s)
W=volume flowrate (m$^3$/s)
A=cross sectional area of the pipe (m$^2$)
Thus V=0.000074/(π×0.004$^2$/4)=5.9 (m/s)

A summary of the results of this calculation is shown in table 1 below.

TABLE 1

| | |
|---|---|
| Coil duty | 1 kW |
| Pipe diameter | 4 mm |
| Liquid flowrate | 0.074 l/s |
| Liquid velocity | 5.9 m/s |
| Pipe length | 5.6 m |
| Pressure drop | 6.9 bar |

The table shows that although the 4 mm diameter coil is capable of operating in a reaction that generates 1 kW of heat, it does so at the expense of very high pressure drop (of the heat transfer fluid). A small increase in process load beyond 1 kW would require even higher flowrates and a longer coil which would result in an unacceptably high pressure drop. Thus under the conditions which have been chosen purely for the purposes of illustration, at a load of 1 kW the 4 mm diameter coil is at the top end of its operating range.

A larger pipe diameter of 5 mm internal bore is therefore selected for the second iteration.

At a flowrate of 0.000074 m$^3$/s through a 5 mm bore pipe, the pressure drop of the heat transfer fluid is 0.42 bar/m (based on a standard pressure drop calculation synthetic heat transfer fluid).

The pipe length is again calculated from the relationship $$L = A/\pi D$$

where
L=pipe length=(m)
A=surface area of pipe (m$^2$)
D=pipe diameter=0.005 (m)
π=3.1416

The required area (A) is determined from the heat transfer capabilities of the pipe using the same formula $$A = q/U \cdot LMTD \ (m^2)$$

as was used in the first iteration.

With the 5 mm coil however, (note the value of U is lower in this case (0.66 kW·m$^{-2}$·K$^{-1}$) this is due to the reduced service fluid velocity (which gives a higher service side boundary layer resistance).

$$A = 1/(0.66 \times 19.6) = 0.077 \ m^2$$

$$L = 0.077/(3.1416 \times 0.005) = 4.9 \ m$$

The pressure drop through the line=4.9×0.42=2.1 bar.

Also the new velocity is calculated as follows: Thus V=0.000074/(π×0.005$^2$/4)=3.8 (m/s)

The result of this second calculation are shown in table 2.

TABLE 2

| | |
|---|---|
| Coil duty | 1 kW |
| Pipe diameter | 5 mm |
| Liquid flowrate | 0.074 l/s |
| Liquid velocity | 3.8 m/s |
| Pipe length | 4.9 m |
| Pressure drop | 2.1 bar |

The 5 mm diameter coil therefore offers good linear velocities and a moderate pressure drop. Such a coil would therefore be useful for the operating conditions for the reaction used for the purposes of this example. The velocity is also well above the minimum preferred value (1 m/s).

To be of practical service, a heat transfer coil needs to operate over a range of conditions as opposed to being limited to one specific heat transfer rate. Table 3 shows the performance of the 5 mm diameter coil under a variety of conditions (for organic process fluid and synthetic heat transfer oil). The one constant in the table is that the temperature change of the heat transfer fluid flowing through the coil ($t_{si}$−$t_{so}$) is always 10° C.

TABLE 3

CALCULATED COIL LENGTHS FOR A 5 mm ø COIL

| Pressure Drop (bar/m) | Heat capacity (W) | Flow (l/s) | Velocity m/s | LMTD 5° C. (m) | LMTD 10° C. (m) | LMTD 15° C. (m) | LMTD 20° C. (m) | LMTD 25° C. (m) |
|---|---|---|---|---|---|---|---|---|
| 0.1 | 457 | 0.033 | 1.7 | 8.9 | 4.4 | 2.9 | 2.2 | 1.8 |
| 0.25 | 761 | 0.055 | 2.8 | 12.4 | 6.2 | 4.2 | 3.0 | 2.5 |
| 0.50 | 1121 | 0.081 | 4.1 | 17.2 | 8.6 | 5.7 | 4.3 | 3.5 |
| 0.75 | 1439 | 0.104 | 5.3 | 20.8 | 10.4 | 6.9 | 5.2 | 4.2 |
| 1.00 | 1660 | 0.120 | 6.1 | 23.6 | 11.8 | 7.9 | 5.9 | 4.8 |

The first column in table 3 shows pressure drop (per metre of coil) through the coil for a given flow rate. The second column gives the heating or cooling capacity of the coil based on the 10° C. temperature change. The third and fourth columns give the volume flow rate and velocity of the liquid. The last five columns give minimum coil lengths required for the quoted LMTD values. The LMTD temperature values quoted at the top of these columns represent the log mean temperature difference between the heat transfer fluid and the process fluid.

It can be seen from table 3 that different coil lengths are used depending on process heat load and log mean temperature difference between the process and service fluids. Table 3 shows that a large temperature difference is beneficial as it requires shorter coil lengths.

From table 3, a good general-purpose coil would be 5.9 metres in length. This would be capable of serving any of the duties contemplated in table 3 where the required coil length was 5.9 metres or less. It would be suitable for a process load of 1.66 kW providing the difference in temperature between process and heat transfer fluid was at least 20° C. Under these conditions the pressure drop through the coil would be 5.9 bar.

The coil also offers adequate heat transfer area and reasonable control response at heat loads down to 0.46 kW. Although low velocities are tolerable the control system becomes increasingly sluggish with low flows. Also low velocities result in a large ratio of thermal mass (of heat transfer fluid) to heat load. This tends to magnify any errors of temperature measurement. High liquid velocity is therefore desirable as it gives faster control response and a better (lower) ratio of thermal mass (of the heat transfer fluid) to heat load.

For the reasons given above, high heat transfer fluid velocities are generally desirable. Very high pressure drops however also introduce greater energy from turbulence and friction. There are also practical equipment constraints on how fast a liquid can be pumped through a pipe. The single coil system of example 1 is useful, but has its limitations.

As example 1 illustrates, a single coil has an optimum operating range. Although it is capable of measuring a range of heat transfer rates, it has its limitations. As table 3 shows, at heat transfer rates above 1121 W, the pressure drop across the coil increases rapidly due to the need for increasingly longer pipes and higher pressure drops per meter of pipe length.

The limitations of the single coil may be illustrated as follows:

A coil 6.2 m long operating with an LMTD (log mean temperature difference between the process fluid and service fluid) of 10° C. has a nominal operating range of 457-1121 W. At maximum load, the pressure drop across the coil would be 1.55 bar. If this coil was to be used with a heat load of 1660 W under the same conditions, it would have to be 11.8 meters long and the corresponding pressure drop would be 11.8 bar. If, under the same conditions, the LMTD was reduced to 5° C., the pipe would need to be 23.6 meters long and the resulting pressure drop would be 23.6 bar.

Although the range of a coil can be increased by varying the inlet temperature ($t_{si}$), there are limitations. If the temperature difference ($t_{si}-t_{so}$) is reduced, the system becomes progressively less accurate due to limitations of the temperature measuring devices. If the temperature difference ($t_{si}-t_{so}$) is expanded too far, there is a risk of freezing the process fluid (or surface boiling or heat damage where heat is being absorbed by the process fluid).

Although service fluid flow and supply temperatures are both parameters that can be varied to alter the operating range, reliable control methods favour using one control parameter at a time (and step changing the other where necessary).

The 5 mm diameter coil illustrated in example 1 gives a turn down ratio of approximately 2.5 (1121/457). If the temperature difference across the coil ($t_{si}-t_{so}$) was increased from 10° C. to 20° C., the turn down ratio could be increased to 5. An alternative method of increasing the operating range of the system is to use multiple coils in a cascade fashion, which provide a variable area heat transfer surface. Such a system is illustrated by the following A method of increasing the operating range of the system is to employ variable area heat transfer according to the present invention and use multiple coils in a cascade fashion. Such a system is illustrated in example 2 in which the principles of coil sizing illustrated in example 1 are applied to a series of coils.

EXAMPLE 2

Example 2 illustrates, the design of variable area heat transfer systems employing multiple coil systems such as those illustrated in FIGS. 2 and 3. As in example 1, the cooling (or heating) coil system controls the process temperature and continuously measures the heat gained or lost using information on mass flowrate through the coil, temperature change ($t_{si}-t_{so}$) and specific heat of the heat transfer fluid.

Example 2 addresses the fact that a reactor might be required to handle exothermic reactions which generate heat in the range of 500 to 15,000 W. A range of this size exceeds the operating capabilities of the single heat transfer coil system illustrated in example 1. Such a reactor can however be effectively operated using multiple coils as illustrated in this example (in this example identical coils each 11.8 m long are used) in a cascade fashion. With one coil operating with the heat transfer fluid at 1.7 m/s, a heat load of 457 W will give a temperature rise in service fluid ($t_{si}-t_{so}$) of 10° C. If, under the same conditions the velocity of the heat transfer fluid is increased to 6.1 m/second the capacity rises to 1,660 W (see table 3). If two coils are used at maximum flow the capacity is 3,320 W. By adding coils in this manner ever greater heat loads can be measured. If, for example, ten coils are used at the maximum flow, the capacity is 16,600 W. This system therefore offers a turndown ratio of approximately 36 (16,600/457). Accordingly, by varying the velocity of the fluid and the number of coils, the heat capacity can be measured with a high degree of accuracy over a wide range.

The devices described so far have turndown capacities of up to 36. In practice, a turndown of 1000 or more may be desirable. This could be important with a batch reaction where the end point needs to be identified with precision. Alternatively, high turndown would be useful for process operations that switch from batch to continuous operation. In other cases, the same piece of equipment might be used on multiple applications of widely varying energy release (or absorption) rates. The individual coil turn down capabilities described above (temperature, flow rate) enable the system to be adapted for different operating conditions. It must be recognised however that in normal operation constant flow and temperature to each conduit is desirable. For this reason a large number of conduits deliver the best representation of variable area control (with all the benefits that brings). Whilst the device previously described has considerable use it has its limitation for this type of application, because an impractical number of coils would be needed. Therefore an alternative embodiment of the invention uses a plurality of coils for varying available heat transfer area as illustrated in example 3.

EXAMPLE 3

Table 4 sets out the heat transfer capacities of a series of coils of varying diameter and length.

TABLE 4

| Coil diameter (mm) | Coil length range (m) | Operating range (W) |
|---|---|---|
| 1 | 0.13-0.6 | 4-22 |
| 2 | 0.9-2.3 | 40-141 |
| 3 | 1.9-4.7 | 118-429 |
| 4 | 3.0-7.8 | 249-913 |
| 5 | 4.4-11.8 | 457-1660 |

In order to arrive at the operating range, as with example 2, the LMTD is taken as 10° C. and $(t_{si}-t_{so})$ as 10° C. The extremes of the ranges set out in columns two and three of table 4 represent the calculated values for minimum and maximum flow of the heat transfer fluid. Minimum flow is that which results in a pressure drop (of service fluid) of 0.1 bar·m$^{-1}$ and maximum flow that which results in a pressure drop (of service fluid) 1 bar·m$^{-1}$.

This combination of coil diameters and lengths provides a system capable of very high turndown rations. For example a six coil reactor can be designed to operate at less than 4 W and up to 5000 W. Table 5 shows the cumulative capacity of 6 coils of varying diameter.

TABLE 5

| Coil number | Coil diameter (mm) | Coil range (W) | Cumulative range (W) |
|---|---|---|---|
| 1 | 1 mm | 4-22 | 4-22 |
| 2 | 1 mm | 4-22 | 4-44 |
| 3 | 2 mm | 40-141 | 4-185 |
| 4 | 3 mm | 118-429 | 4-614 |
| 5 | 5 mm | 457-1660 | 4-2274 |
| 6 | 5 mm | 457-1660 | 4-3934 |

Each coil is sized for the maximum length shown in table 4. The nominal turndown ratio of the six coils is 984.

If $(t_{si}-t_{so})$ is stepped down to 5° C. when a single 1 mm diameter coil is operating, the nominal turndown ratio is increased to 1967 (2-3934 W).

If $(t_{si}-t_{so})$ is stepped up to 20° C. when all the coils are operating the nominal turndown ratio is increased to 3934 (2-7868 W).

The six-coil arrangement described above offers a good operating range. To achieve smooth heat flow transition as coils open up however is more difficult to achieve. There are two options on a six-coiled system. Firstly the supply pressure or temperature can be varied to provide intermediate heating/cooling capacities. Alternatively the on/off valves can be operated in a more complex sequence. The preferred solution however is to use more coils. For example a system might use 10 of 1 mm ϕ coils 10 of 2 mm diameter coils and 10 of 3 mm ϕ coils.

The invention therefore enables a very large operating range with simple reactor design.

In some cases, rigorous analysis may require greater overlap (in terms of operating range) to ensure that pipes when opened can operate in the preferred fluid velocity range.

The invention can be used to improve the operation of commercial chemical and physical reaction systems. It can however also be used to provide considerably smaller reaction systems with comparable commercial throughput. For example the invention enables reduction of reactor size by a factor of 10 and, in some instances, a factor of 100 or greater. In particular it can be applied to current commercial
- batch organic synthesis reactions currently carried out in reactors of 10 to 20,000 liters.
- bulk pharmaceutical synthesis reactions currently carried out in reactions of 10 to 20,000 liters.
- batch polymerisation reactions currently carried out in reactors of 10 to 20,000 liters.
- batch synthesis reactions of 10 to 20,000 liters currently used for unstable materials (compounds susceptible to self-accelerating runaways).
- batch inorganic synthesis reactions currently carried out in reactions of 10 to 20,000 liters.

The techniques may also be useful in larger scale chemical and petrochemical operations.

This technology will also be of value as an alternative calorimetry for research and development applications. In this capacity, it would be used for isothermal calorimetry in equipment of 1 mil to 10 liters capacity. This technology can also be used for small-scale reaction applications. In this capacity it would be used for reaction equipment of 1 ml to 10 ml capacity.

The invention claimed is:

1. A batch reaction system comprising:
a reaction vessel containing a process fluid;
a plurality of heat transfer elements having a passageway therethrough for the passage of heat transfer fluid, said plurality of elements disposed about and in contact with a surface of said reaction vessel to provide a heat transfer surface between the process fluid and each of said plurality of elements;

at least one sensor that detects a change of temperature of said heat transfer fluid that enters and exits said plurality of heat transfer elements;

a flow rate sensor that detects the flow rate of the heat transfer fluid passing through said heat transfer elements; wherein heat generated or absorbed by the process fluid in the reaction vessel is calculated from said change of temperature of the heat transfer fluid and a flow rate of said heat transfer fluid;

a valve system in fluid communication each of with said plurality of elements;

wherein said valve system acts to progressively provide or prevent access of heat transfer fluid to the plurality of heat transfer elements in cascade fashion and thereby control the number of heat transfer elements in effective heat transfer contact with the reaction vessel.

2. A reaction system according to claim 1, wherein said plurality of heat transfer elements comprise a plurality of pipes or coils.

3. A reaction system according to claim 2, in which the walls of each of the plurality of pipes or coils are from ½ to 4 mm thick.

4. A reaction system according to claim 1, in which the available heat transfer surface of the plurality of heat transfer elements is controlled so as to be sufficient to ensure that a temperature difference $(t_{si}-t_{so})$ of more than 1° C. is observed in the heat transfer fluid as it passes across the reaction.

5. A reaction system according to claim 4, in which the temperature difference is more than 5° C.

6. A reaction system according to claim 1, in which the plurality of heat transfer elements comprises a plurality of pipes or coils having a diameter to length relationship calculated by first calculating the heat transfer area required using the formula $$U \cdot A \cdot LMTD = m \cdot Cp \cdot (t_{si}-t_{so}) \text{ (kW)}$$

where
- U=overall heat transfer coefficient (kW·m$^{-2}$·K$^{-1}$)
- A=heat transfer area (m$^2$)
- m=mass flow rate of heat transfer fluid (kg/s)
- LMTD=log mean thermal difference between service and process fluids (° C.)
- Cp=specific heat of heat transfer fluid (kJ·kg$^{-1}$K$^{-1}$)
- $(t_{si}-t_{so})$=temperature (° C.) change in the heat transfer fluid between inlet and outlet.

7. A reaction system according to claim 1, in which the plurality of heat transfer elements comprise a plurality of heat transfer pipes or coils each of which has a diameter and length relationship designed to provide a certain degree of heat transfer and in which the plurality of pipes or coils may be brought into and out of operation according to the measured heat generated or absorbed by the reaction.

8. A reaction system according to claim 1, wherein said system comprises 10 or more heat transfer elements.

9. A reaction system according to claim 1, wherein said output signal from the controller is used to determine the heat generated or absorbed by the reaction system.

10. A reaction system according to claim 9, wherein the determination of heat generated or absorbed by the reaction system is used to control an area of said heat transfer surface between a conduit and said process fluid.

11. A reaction system according to claim 1, wherein:
 (i) the average temperature difference between said heat transfer fluid and said process fluid is from 1° C. to 1000° C.;
 (ii) The temperature differential of the heat transfer fluid across the reaction system is at least 0.1° C.; and/or
 (iii) The linear velocity of the transfer fluid is at least 0.01 meters/second.

* * * * *